US006689762B1

(12) United States Patent
Avramis et al.

(10) Patent No.: US 6,689,762 B1
(45) Date of Patent: Feb. 10, 2004

(54) COMPOSITION AND METHODS FOR TREATMENT OF HIV INFECTION

(75) Inventors: Vassilios I. Avramis, Sylmar, CA (US); Lewis Cohen, Pottstown, PA (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 09/370,390

(22) Filed: Aug. 6, 1999

Related U.S. Application Data

(63) Continuation-in-part of application No. PCT/US99/02480, filed on Feb. 9, 1999.
(60) Provisional application No. 60/074,066, filed on Feb. 9, 1998, now abandoned.

(51) Int. Cl.$^7$ .......................... A01N 43/04; A61K 31/70
(52) U.S. Cl. ................... 514/50; 514/49; 514/51
(58) Field of Search .................. 514/49, 50, 51

(56) References Cited

FOREIGN PATENT DOCUMENTS

| FR | 0250335 A1 | 6/1987 | .......... A61K/37/54 |
|----|-----------|--------|----------------------|
| FR | 0 250 335 A1 | 6/1987 | .......... A61K/37/54 |
| WO | WO98/56410 | 12/1998 | |

OTHER PUBLICATIONS

Bianchi et al., Proc. Natl. Acad. Sci, vol. 91, pp 8403–8407, Aug. 1994.*
Collier et al. New England Journal of Medicine, vol. 334, No. 16, pp. 1011–1017, Apr. 1996.*
Giacca et al., AIDS Research and Human Retrovinses, vol. 12, No. 8, May 1996.*
Chon et al., Proc. Natl. Acad. Sci., vol. 94, pp 13193–13197, Nov. 1997.*
Levien et al., "Review of Pegaspargase and Oral Pilocarpine", *Hosp Pharm.*, 30(1), 52, 54–59 (1995).
Holle, "Pegaspargase: An Alternative?" *Annul. Pharmacother.*, 31, 616–624 (May 1997).
Gusselbracht et al., "Human Immunodeficiency Virus–Related Lymphoma Treatment With Intensive Combination Chemotherapy", *Amer. J. Med.*, 95, 188–196 (1993).
Monfardini et al., "Treatment of acquired immunodeficiency syndrome (AIDS)—related cancer," *Cancer Treat. Rev.*, 20, 149–172 (1994).
Tupule et al., "PEG–L–Asparaginase Has Activity in Relapsed/Refactory Aids–Related Lymphomas,"*JAIDS*, 21(1), A38 (May 1, 1999).
Tupule et al., "Prelimianry Results of PEG–L–Asparaginase (Oncaspar) in Treatment of Relapsed/Refractory Aids–Related Lymphomas,"*J. Aids Hum.Retrovir.*, 17(4), A31 (Apr. 1, 1998).
Tupule et al., "Prelimianry Results of PEG–L–Asparaginase (Oncaspar) in Treatment of Relapsed/Refractory Aids–Related Lymphomas,"*Blood*, 92(10), Suppl. 1, Part 1–2, 240B–241B (Nov. 15, 1998).
*Catalog* (Shearwater Corp., Huntsville, AL, 2001).
Ettinger et al. "Acute Lymphoblastic Leukaemia, A Guide to Asparaginase and Pegaspargase Therapy," *BioDrugs*, 7(1), 30–39 (Jan. 1997).
Bianchi et al., "Inhibition of ribonucleotide reductase by 2'-substituted deoxycytidine analogs: Possible application in AIDS treatment" *Proc. Natl. Acad. Sci. USA*, 91, 8403–8407 (1994).
Malogolowkin et al., "Successful CSF Asparagine (Asn) Depletion Following Administration of PEG–Asparaginase (PEG–ASNase) in Children with Acute Lymphoblastic Leukemia (ALL) and Isolated CNS Relapse," *Proc. ASCO*, 17, 2035 (1998).

* cited by examiner

*Primary Examiner*—James O. Wilson
*Assistant Examiner*—Patrick Lewis
(74) *Attorney, Agent, or Firm*—Muserlian, Lucas & Mercanti, L.L.P.

(57) ABSTRACT

Method of inhibiting or treating Human Immunodeficiency Virus (HIV) infection, comprising administering to a patient in need thereof an effective amount of a pharmaceutically acceptable composition comprising a PEG-ASNase compound or asparaginase, and optionally at least one compound selected from the group consisting of protease inhibitor compounds, ribonucleotide reductase inhibitor compounds and HIV reverse transcriptase inhibitor compounds.

12 Claims, 13 Drawing Sheets

COMPOSITION AND METHODS FOR TREATMENT OF HIV INFECTION

This application is a continuation-in-part of International Patent Application No. PCT/US99/02480, filed on Feb. 9, 1999, which is, in turn, a continuation-in-part of U.S. Provisional Patent Application No. 60/074,066, filed Feb. 9, 1998, now abandoned.

FIELD OF THE INVENTION

The invention is directed to a pharmaceutical composition comprising a PEG-ASNase compound or a pharmaceutically acceptable salt thereof, and optionally at least one compound selected from the group consisting of protease inhibitor compounds, ribonucleotide reductase inhibitor compounds and HIV reverse transcriptase inhibitor compounds, and a pharmaceutically acceptable carrier. The invention is also directed to a method of inhibiting or treating Human Immunodeficiency Virus (HIV) infection, comprising administering to a patient in need thereof a therapeutically effective amount of a PEG-ASNase compound or a pharmaceutically acceptable salt thereof, and optionally at least one compound selected from the group consisting of protease inhibitor compounds, ribonucleotide reductase inhibitor compounds and HIV reverse transcriptase inhibitor compounds, or a pharmaceutically acceptable salt thereof.

The human immunodeficiency virus (HIV) is a retrovirus and is the agent of the complex disease that includes progressive destruction of the immune system (acquired immune deficiency syndrome; AIDS) and degeneration of the central and peripheral nervous system. This retrovirus is previously known as LAV, HTLV-III, or ARV. There have been various therapies to treat HIV infection, including therapies with combination drug regimens. Protease inhibitor compounds in combination with reverse transcriptase (RT) inhibitor compounds have shown success both in vitro and in vivo in patients infected with the virus. Protease inhibitor compounds interfere with the production of new infectious virus. A common feature of the HIV retrovirus replication is extensive post-translational processing of precursor poly-proteins by a virally encoded protease to generate mature viral proteins required for virus assembly and function. Inhibition of this processing prevents the production of new infectious virus.

Inhibition of the HIV protease by protease inhibitors may prevent proviral integration of infected T-lymphocytes during the early phase of the HIV-1 life cycle, as well as inhibit viral proteolytic processing during its late stage. HIV protease inhibitors have been extensively reviewed (A. Tomasselli et al., Chimica Oggi, 6–27 20 (1991) and T. Meek, J. Enzyme Inhibition 6: 65–98 (19.92). Retroviral replication routinely features post-translational processing of polyproteins. This processing is accomplished by virally encoded HIV protease enzymes. This post-translational process yields mature polypeptides that will subsequently aid in the formation and function of infectious viruses. If this molecular processing is inhibited, then the normal production of HIV is terminated. Therefore, it has been discovered that inhibitors of HIV protease may function as anti-HIV viral agents.

Retroviruses are widely distributed in vertebrates and are known to cause a variety of diseases in man and animals including HIV, leukemias and lymphomas. The entire retrovirus family is characterized by the presence of a unique enzyme, reverse transcriptase (RT), which transcribes the viral genomic RNA into a double-stranded DNA copy. Therefore, considerable efforts are being directed toward the control of HIV by means of inhibition of HIV-reverse transcriptase, required for replication of the virus. (V. Merluzzi et al., "Inhibition of the HIV-1 Replication by a Nonnucleoside Reverse Transcriptase Inhibitor", Science, 25, 1411 (1990)). For example, a currently used therapeutic compound, AZT, is an inhibitor of the viral reverse transcriptase (U.S. Pat. No. 4,724,232). Unfortunately, many of these compounds suffer from toxicity problems, lack of bioavailability or are short lived in vivo, viral resistance, or combinations thereof.

It is also known that the inhibition of HIV-reverse transcriptase (HIV-RT) by nucleoside analogue drug combinations indicate that they cannot alone inhibit the RT function completely, but instead can lead to the emergence of drug resistant viral strain. These strains of escape mutants repopulate and render nucleoside analogue therapy ineffective. The addition of protease inhibitor compounds to known nucleoside analogue combination therapies has helped to reduce the viral burden for a prolonged period of time.

Ribonucleotide reductase is an allosterically regulated enzyme that converts the nucleoside diphosphates to their corresponding deoxynucleoside diphosphates through a complex regulatory mechanism involving one or several electron transfer pathways. (Holmgren A. Hydrogen donor system for *E. Coli* Ribonucleoside diphosphate reductase dependent upon glutathione, Proc. Natl. Acad. Sci. USA, 1976, 73, 2275–9; Therlander L., Reductase of Ribonucleotides, Ann. Rev. Biochem. 1979,46, 133–58; Ashley G W, Stubbe J., Current ideas on the chemical mechanism of ribonucleotide reductase, Pharmac. Ther. 1985, 30, 301–29; Stubbe J., Ribonucleotide Reductase: Amazing and confusing, J. Biol. Chem. 1990, 265, 5329–32.) Reduction of the ribonucleotide by ribonucleotide reductase enables the DNA ploymerases to utilize the deoxyribonucleotides (dNTPs) during the process of DNA replication. Ribonucleotide reductase activity is well coordinated to the process of cellular proliferation and is markedly increased in the late G1 and the early S-Phase when the bulk of DNA synthesis occurs. (Corey J. G., Whitford Jr. T. W., Ribonucleotide reductase and DNA synthesis in Ehrlich ascites tumor cancer cells, Cancer Res., 1972, 32, 1301–6; Hammerstan E, Reichard P., Saluste E., Pyrimidine nucleosides as precursors of pyrimidines in polynucleotides, J. Biol. Chem., 1950, 183, 105–109.) The important role of ribonucleotide reductase in the synthesis of DNA makes it a target for chemotherapeutic agents. There has recently been found a class of 2-hydroxy-1H-isoindole-1,3-dione (HISID) which have been shown to have ribonucleotide reductase inhibitor activity (Nandy P, Lien E J, Avramis V I, Acta Oncologica, 33, 8, 953–61, 1994; Nandy P, Lien E J, Avramis V I, Rec Adv Chemoth 1:995–996, 1994; Nandy P, Lien E J, Avramis V I, Med. Chem. Res. 1995, 5:664–679.)

PEG-asparaginase (the polyethylene glycosylated form of *E.coli*-ASP) has been shown to be useful as a chemotherapeutic agent. In particular, PEG-asparaginase has been found to be an alternative preparation with a longer circulating half-life than *E.coli* L-asparaginase and has been useful in multiagent chemotherapy for childhood acute lymphoblastic leukemia. (Ettinger L J, Ettinger A G, Avramis V I, Gaynon P S, BioDrugs, 7, 1, 30–39, 1997). Also, PEG-ASNase may increase the anti-leukemic effect in isolated CNS relapse. (Malgolowkin M, Ortega S, Carcich D A, Steele D, Tischer D, Franklin J, Nandy P, Periclou A, Cohen L J, Avramis V I, Proceedings of ASCO, 17, 1998.)

PEG-ASNase is a conjugate of asparaginase with polyethylene glycol. This conjugation occurs through pegylation, a process in which polypeptides, such as enzymes and hormones, are coupled to polyethylene glycol so as to produce a physiologically active non-immunogenic water-soluble polypeptide composition. The polyethylene glycol protects the polypeptide from loss of activity and the composition can be injected into the mammalian circulatory system with substantially no immunogenic response. The process of pegylation is described in detail in U.S. Pat. No. 4,179,337, entitled "Non-immunogenic Polypeptide", filed Jul. 28, 1977 and issued Dec. 18, 1979, which is incorporated by reference in its entirety herein. Covalent attachment of the polymer to the peptide is affected often by reacting PEG-succinimide derivatives with amino groups on the exterior of protein molecules. Other methods are also disclosed in U.S. Pat. No. 4,179,337, in Pollack et al., JACS, 298, 289 (1976), U.S. Pat. No. 4,847,325 and elsewhere in the art.

SUMMARY OF THE INVENTION

Applicants have discovered that PEG-asparaginase (PEG-ASNase) effectively works alone and synergistically works in combination with one or more of the following: protease inhibitor compounds, HIV reverse transcriptase inhibitor compounds, or ribonucleotide reductase inhibitor compounds, to treat infection by HIV.

Accordingly, in its principle aspect, this invention is directed to a pharmaceutical composition comprising a PEG-ASNase compound and optionally at least one compound selected from the group consisting of: protease inhibitor compounds, ribonucleotide reductase inhibitor compounds and HIV reverse transcriptase inhibitor compounds, and a pharmaceutically acceptable carrier. The invention is also directed to a method of inhibiting or treating Human Immunodeficiency Virus (HIV) infection, comprising administering to a patient in need thereof a therapeutically effective amount of a PEG-ASNase compound or a pharmaceutically acceptable salt thereof, and optionally at least one compound selected from the group consisting of protease inhibitor compounds, ribonucleotide reductase inhibitor compounds and HIV reverse transcriptase inhibitor compounds, or a pharmaceutically acceptable salt thereof.

DETAILED DESCRIPTION OF THE INVENTION

Figure 1:
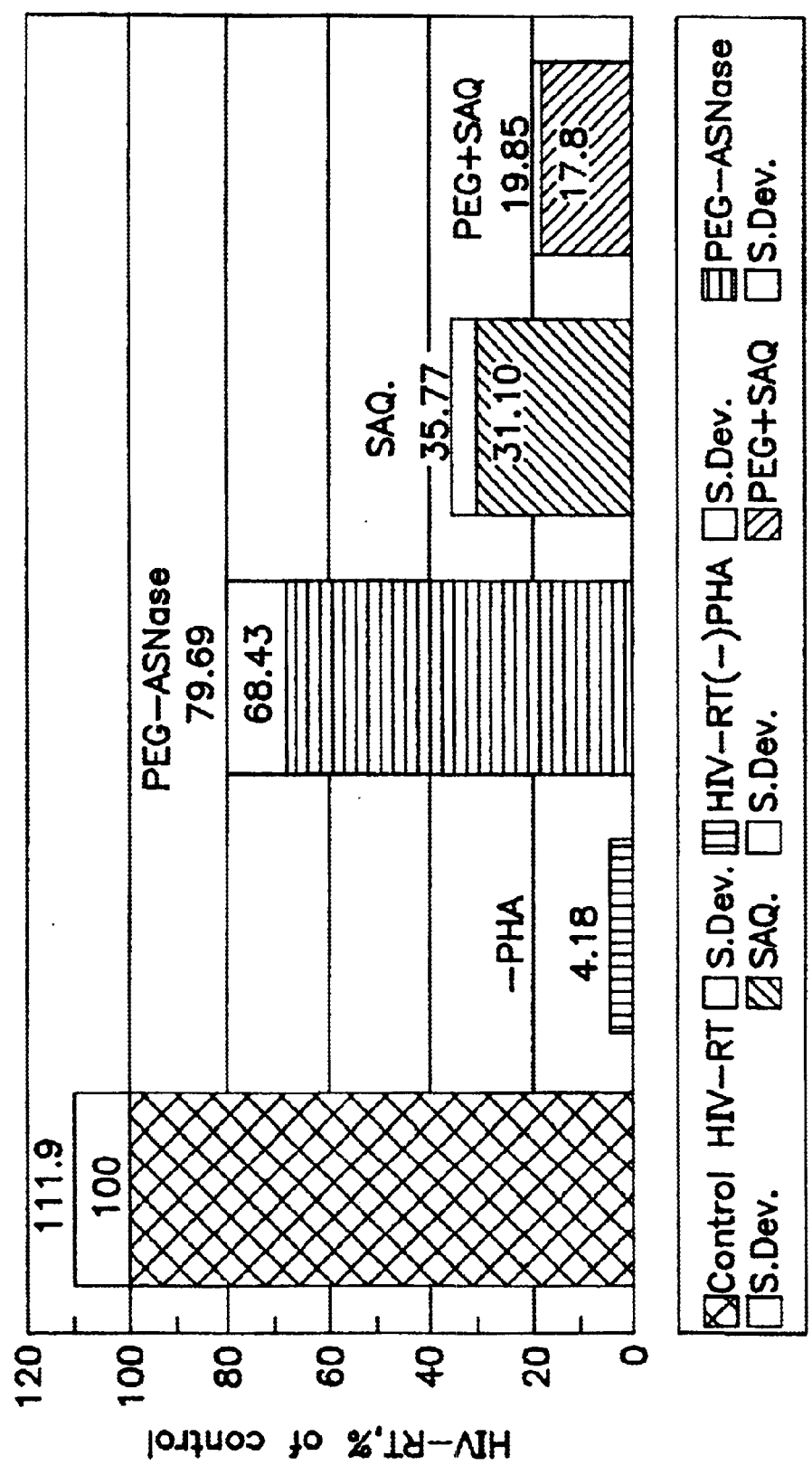
FIG. 1 represents the inhibition of HIV-RT in CEM/0 T-cells (±PHA) treated with IC50 concentrations of PEG-ASNase or Saquinavir (SAQ) alone or in their combination.

As used above, and throughout the description of the invention, the following terms, unless otherwise indicated, shall be understood to have the following meanings:

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo or cycloalkyl group. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 12 carbon atoms in the chain. Most preferred alkyl groups have 1 to about 3 carbon atoms in the chain. Branched means that one or more lower alkyl groups such as methyl, ethyl or propyl are attached to a linear alkyl chain. "Lower alkyl" means about 1 to about 3 carbon atoms in the chain which may be straight or branched. The alkyl may be substituted with one or more "alkyl group substituents" which may be the same or different, and include halo, cycloalkyl, hydroxy, alkoxy, amino, acylamino, aroylamino, carboxy, alkoxycarbonyl, aralkoxycarbonyl, heteroaralkoxycarbonyl or $Y^1Y^2NCO$—, wherein $Y^1$ and $y^2$ are independently hydrogen, optionally substituted alkyl, optionally substituted aryl, optionally substituted aralkyl or optionally substituted heteroaralkyl, or $Y^1$ and $Y^2$ taken together with the N through which $Y^1$ and $Y^2$ are linked form a 4 to 7 membered heterocyclyl. Exemplary alkyl groups include methyl, trifluoromethyl, cyclopropylmethyl, cyclopentylmethyl, ethyl, n-propyl, i-propyl, n-butyl, i-butyl, n-pentyl, 3-pentyl, methoxyethyl, carboxymethyl, formyl, methoxycarbonylethyl, benzyloxycarbonylmethyl, pyridylmethyloxycarbonylmethyl. Preferred alkyl substituents are halo, hydroxy, alkoxy, amino, acylamino, aroylamino, carboxy, alkoxycarbonyl, aralkoxycarbonyl, heteroaralkoxycarbonyl, sulfonyl, sulfinyl, acyl, alkanoyl, or $Y^1Y^2NCO$—.

"Alkylthio" means an alkyl-S— group wherein the alkyl group is as herein described. Exemplary alkylthio groups include methylthio, ethylthio, i-propylthio and heptylthio.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$— group wherein the alkyl group is as defined above. Preferred groups are those wherein the alkyl group is lower alkyl.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl and decynyl.

"Analogue" means a compound which comprises a chemically modified form of a specific compound or class thereof, and which maintains the pharmaceutical and/or pharmacological activities characteristic of said compound or class.

"Aralkoxy" means an aralkyl-O— group wherein the aralkyl groups is as herein described. Exemplary aralkoxy groups include benzyloxy and 1- or 2-naphthalenemethoxy.

"Aralkoxycarbonyl" means an aralkyl-O—CO— group wherein the aralkyl groups is as herein described. An exemplary aralkoxycarbonyl group is benzyloxycarbonyl.

"Aralkyl" means an aryl-alkyl— group wherein the aryl and alkyl are as herein described. Preferred aralkyls contain a lower alkyl moiety. Exemplary aralkyl groups include benzyl, 2-phenethyl and naphthlenemethyl.

"Aralkylthio" means an aralkyl-S— group wherein the aralkyl group is as herein described. An exemplary aralkylthio group is benzylthio.

"Aryloxycarbonyl" means an aryl-O—CO— group wherein the aryl group is as defined herein. Exemplary aryloxycarbonyl groups include phenoxycarbonyl and naphthoxycarbonyl.

"Aroylamino" is an aroyl-NH— group wherein aroyl is as defined herein.

"Aroyl" means an aryl-CO— group wherein the aryl group is as herein described. Exemplary groups include benzoyl and 1- and 2-naphthoyl.

"Aryl" means an aromatic monocyclic or multicyclic ring system of about 6 to about 14 carbon atoms, preferably of about 6 to about 10 carbon atoms. The aryl is optionally substituted with one or more "ring system substituents" which may be the same or different, and are as defined herein. Exemplary aryl groups include phenyl or naphthyl, or phenyl substituted or naphthyl substituted.

"Aryldiazo" means an aryl-diazo-group wherein the aryl and diazo groups are as defined herein.

"Aryloxy" means an aryl-O— group wherein the aryl group is as defined herein. Exemplary groups include phenoxy and 2-naphthyloxy.

"Arylsulfonyl" means an aryl-$SO_2$— group wherein the aryl group is as defined herein.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Carboxy" means a HO(O)C— (carboxylic acid) group.

"Compounds of the invention", and equivalent expressions, are meant to embrace compounds of the invention as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. The cycloalkenyl is optionally substituted with one or more "ring system substituents" which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms. The cycloalkyl is optionally substituted with one or more "ring system substituents" which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Diazo" means a bivalent —N=N— radical.

"Effective amount" means an amount of a compound/composition according to the present invention effective in producing the desired therapeutic effect.

"Electron withdrawing group" as defined herein refers to a group that will draw electrons to itself more than a hydrogen atom would if it occupied the same position in the molecule. See, J. March, Advanced Organic Chemistry, 3rd Ed., John Wiley & Sons P. 17 (1985). They include such groups as nitro, monohaloalkyl, dihaloalkyl, trihaloalkyl (e.g., $CF_3$), halogen, formyl, alkylsulfonyl, alkylsulfinyl, and the like. Preferably halogen.

"Formulations suitable for nasal or inhalational administration" means formulations which are in a form suitable to be administered nasally or by inhalation to a patient. The formulation may contain a carrier, in a powder form, having a particle size for example in the range 1 to 500 microns (including particle sizes in a range between 20 and 500 microns in increments of 5 microns such as 30 microns, 35 microns, etc.) Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

"Formulations suitable for oral administration" means formulations which are in a form suitable to be administered orally to a patient. The formulations may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

"Formulations suitable for parenteral administration" means formulations which are in a form suitable to be administered parenterally to a patient. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

"Formulations suitable for rectal administrations" means formulations which are in a form suitable to be administered rectally to a patient. The formulation is preferably in the form of suppositories which can be prepared by mixing the compounds useful according to this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

"Formulations suitable for systemic administration" means formulations which are in a form suitable to be administered systemically to a patient. The formulation is preferably administered by injection, including transmuscular, intravenous, intraperitoneal, and subcutaneous. For injection, the compounds useful according to the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

"Formulations suitable for topical administration" means formulations which are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

"Formulations suitable for vaginal administration" means formulations which are in a form suitable to be administered vaginally to a patient. The formulation may be presented as pessaries, tampons, creams, gels, pastes, foams or spray formulations containing in addition to the active ingredient such carriers as are known in the art to be appropriate.

"Heteroaralkoxycarbonyl" means an heteroaralkyl-O—CO— group wherein the heteroaralkyl groups is as herein described. An exemplary heteroaralkoxycarbonyl group is thienylmethylcarbonyl.

"Heteroaralkyl" means a heteroaryl-alkyl-group wherein the heteroaryl and alkyl are as herein described. Preferred heteroaralkyls contain a lower alkyl moiety. Exemplary heteroaralkyl groups may contain thienylmethyl, pyridylmethyl, imidazolylmethyl and pyrazinylmethyl.

"Heteroaralkylthio" means an heteroaralkyl-S— group wherein the heteroaralkyl group is as herein described. An exemplary heteroaralkylthio group is pyridylmethylthio.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The "heteroaryl" may also be substituted by one or more "ring system substituents" which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo [2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. Preferred heteroaryl groups include pyrazinyl, thienyl, pyridyl, pyrimidinyl, isoxazolyl and isothiazolyl.

"Heteroaryldiazo" means an heteroaryl-diazo-group wherein the heteroaryl and diazo groups are as defined herein.

"Heteroarylsulfonyl" means an aryl-$SO_2$— group wherein the heteroaryl group is as defined herein.

"Heteroarylsulfinyl" means an aryl-SO— group wherein the heteroaryl group is as defined herein.

"Heteroarylthio" means an aryl-S— group wherein the heteroaryl group is as herein described. Exemplary heteroarylthio groups include pyridylthio and pyrimidinylthio.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more ring system substituent, wherein the "ring system substituent" is as defined herein. The nitrogen atom of an heterocyclenyl may be a basic nitrogen atom. The nitrogen or sulphur atom of the heterocyclenyl may also be optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydrofuranyl. Preferred is dihydrofuranyl. An exemplary multicyclic oxaheterocyclenyl group is 7-oxabicyclo[2.2.1]heptenyl. Preferred monocyclic thiaheterocycleny rings include dihydrothiophenyl and dihydrothiopyranyl; more preferred is dihydrothiophenyl. Preferred ring system substituents include amidino, halogen, hydroxy, alkoxycarbonylalkyl, carboxyalkyl or $Y^1Y^2N$— as defined herein.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more "ring system substituents" which may be the same or different, and are as defined herein. The nitrogen atom of an heterocyclyl may be a basic nitrogen atom. The nitrogen or sulphur atom of the heterocyclyl may also be optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Preferred heterocyclyl group substituents include amidino, halogen, hydroxy, alkoxycarbonylalkyl, carboxyalkyl or $Y^1Y^2N$— as defined herein.

"Hydrate" means a solvate wherein the solvent molecule (s) is/are $H_2O$.

"Hydroxyalkyl" means a HO-alkyl-group wherein alkyl is as herein defined. Preferred hydroxyalkyls contain lower alkyl. Exemplary hydroxyalkyl groups include hydroxymethyl and 2-hydroxyethyl.

"Hygroscopicity" means sorption, implying an acquired amount or state of water sufficient to affect the physical or chemical properties of the substance (Eds. J. Swarbrick and J. C. Boylan, Encyclopedia of Pharmaceutical Technology, Vol. 10, p. 33).

"Liquid dosage form" means the dose of the active compound to be administered to the patient is in liquid form, for example, pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

"MISID (PL-7)" means a compound of formula I, wherein R1 is a methyl group; and R2 is an isopropyl group.

"Modulate" means the ability of a compound to either directly (by binding to the receptor as a ligand) or indirectly (as a precursor for a ligand or an inducer which promotes production of a ligand from a precursor) induce expression of gene(s) maintained under hormone control, or to repress expression of gene(s) maintained under such control.

"Patient" includes both human and other mammals.

"PEG-ASNase" means the protein synthesis inhibitor compound, asparaginase, conjugated with polyethylene glycol (PEG). The polyethylene glycol preferably has an average molecular weight between about 1000 and 100,000 daltons, more preferably between 4000 and 40,000 daltons, depending, for example, on the molecular weight of the particular protein synthesis inhibitor compound employed. Since the object of the modification is to obtain a conjugated protein with retained biological activity, with enhanced in vivo half-life over the unconjugated protein synthesis inhibitor compound, and with reduced immunogenicity, the molecular weight of the polymer will be chosen to optimize these conditions. Preferably the PEG homopolymer is substituted at one end with an alkyl group, but it may also be unsubstituted. Preferably the alkyl group is a $C_1$–$C_4$ alkyl group, and most preferably a methyl group. Preferably, the polymer is a monomethyl-substituted PEG homopolymer and has a molecular weight of about 4000 to 40,000 daltons. Most preferably, PEG-ASNase is the compound sold under the name ONCASPAR by Rhône-Poulenc Rorer.

"Pharmaceutical composition" means a composition comprising a compound of the invention and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monosterate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, dicalcium phosphate phosphate. Examples of disintegrating agents include starch, alginic acids and certain complex silicates. Examples of lubricants include magnesium stearate, sodium lauryl sulphate, talc, as well as high molecular weight polyethylene glycols.

"Pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

"Pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

"Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the invention, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larse,n and H. Bundgaard, ed., Chapter 5; "Design and Applications of Prodrugs" p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example S. M. Berge, et al., "Pharmaceutical Salts," J. Pharm. Sci., 66: p.1–19 (1977) which is incorporated herein by reference.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Ring system substituents" mean substituents attached to aromatic or non-aromatic ring systems inclusive of hydrogen, alkylaryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, $Y^1Y^2N-$, $Y^1Y^2N$-alkyl-, $Y^1Y^2NCO-$ or $Y^1Y^2NSO_2-$, wherein $Y^1$ and $Y^2$ are independently hydrogen, optionally substituted alkyl, optionally substituted aryl, optionally substituted aralkyl or optionally substituted heteroaralkyl, or for where the substituent is $Y^1Y^2N-$, then one of $Y^1$ and $Y^2$ may be acyl or aroyl as defined herein and the other of $Y^1$ and $Y^2$ is as defined previously, or for where the substituent is $Y^1Y^2NCO-$ or $Y^1Y^2NSO_2$, $Y^1$ and $Y^2$ may also be taken together with the N atom through which $Y^1$ and $Y^2$ are linked to form a 4 to 7 membered heterocyclyl or heterocyclenyl. When a ring system is saturated or partially saturated, the "ring system substituents" further include, methylene ($H_2C=$), oxo($O=$), thioxo($S=$).

"Solid dosage form" means the dosage form of the compound useful according to the invention is solid form, for example capsules, tablets, pills, powders, dragees or granules. In such solid dosage forms, the compound useful according to the invention is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound(s) useful according to the invention in a certain part of the intestinal tract in a delayed manner.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

In a specific embodiment, the term "about" or "approximately" means within 20%, preferably within 10%, and more preferably within 5% of a given value or range.

Preferred Embodiments

A preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound and at least one protease inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound and at least one HIV reverse transcriptase inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound and at least one ribonucleotide reductase inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound, at least one protease inhibitor compound and at least one ribonucleotide reductase inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound, at least one protease inhibitor compound and at least one HIV reverse transcriptase inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound, at least one ribonucleotide reductase inhibitor compound and at least one HIV reverse transcriptase inhibitor compound.

Another preferred embodiment according to the invention is a method of inhibiting or treating Human Immunodeficiency Virus (HIV) infection, comprising administering to a patient in need thereof an effective amount of a pharmaceutically acceptable composition comprising a PEG-ASNase compound, at least one protease inhibitor compound, at least one ribonucleotide reductase inhibitor compound and at least one HIV reverse transcriptase inhibitor compound.

Another preferred embodiment according to the invention is a method of inhibiting or treating Human Immunodeficiency Virus (HIV) infection, comprising administering to a patient in need thereof a therapeutically effective amount of a PEG-ASNase compound and at least one compound selected from the group consisting of protease inhibitor compounds, ribonucleotide reductase inhibitor compounds and HIV reverse transcriptase inhibitor compounds.

A preferred embodiment according to the invention is a method of inhibiting or treating Human Immunodeficiency Virus (HIV) infection, comprising administering to a patient in need thereof an effective amount of a pharmaceutically acceptable composition comprising asparaginase.

Another preferred embodiment according to the invention is a method of inhibiting or treating Human Immunodeficiency Virus (HIV) infection, comprising administering to a patient in need thereof an effective amount of a pharmaceutically acceptable composition comprising asparaginase and at least one compound selected from the group consisting of protease inhibitor compounds, ribonucleotide reductase inhibitor compounds and HIV reverse transcriptase inhibitor compounds.

Another preferred embodiment according to the invention is a method of inhibiting or treating Human Immunodeficiency Virus (HIV) infection, comprising administering to a patient in need thereof an effective amount of a pharmaceutically acceptable composition comprising at least one ribonucleotide reductase inhibitor compound of formula I $$\text{(I)}$$

wherein
R1 is alkyl, alkenyl, alkynyl or an electron withdrawing group; and
R2 is alkyl, alkenyl, alkynyl; or
a pharmaceutically acceptable salt thereof, an N-oxide thereof, a solvate thereof, an acid bioisostere thereof, or prodrug thereof.

Another preferred embodiment according to the invention is a method of inhibiting the production, or limiting the spread, of HIV comprising exposing a cell population infected with HIV to an effective amount of a PEG-ASNase compound or asparaginase, and optionally at least one compound selected from the group consisting of protease inhibitor compounds, ribonucleotide reductase inhibitor compounds and HIV reverse transcriptase inhibitor compounds.

Another preferred embodiment according to the invention is a method of inhibiting HIV reverse transcriptase activity, comprising contacting HIV reverse transcriptase with a composition comprising a PEG-ASNase compound or asparaginase, and optionally at least one compound selected from the group consisting of protease inhibitor compounds, ribonucleotide reductase inhibitor compounds and HIV reverse transcriptase inhibitor compounds.

Another preferred embodiment according to the invention is a method of inhibiting HIV reverse transcriptase activity, comprising contacting HIV reverse transcriptase with a composition comprising a compound of formula I.

Another preferred embodiment according to the invention is a method of inhibiting HIV reverse transcriptase activity, comprising contacting HIV reverse transcriptase with a composition comprising MISID having the formula Another preferred embodiment according to the invention is a method of inhibiting HIV reverse transcriptase activity, comprising contacting HIV reverse transcriptase with a composition comprising a PEG-ASNase compound.

Another preferred embodiment according to the invention is method of selectively inhibiting HIV-RNA production comprising exposing a cell population infected with HIV to a pharmaceutically acceptable composition comprising a PEG-ASNase compound and at least one protease inhibitor compound.

Another preferred embodiment according to the invention is method of selectively inhibiting HIV-RNA production comprising exposing a cell population infected with HIV to a pharmaceutically acceptable composition comprising a PEG-ASNase compound and Saquinavir.

Another preferred embodiment according to the invention is a method of inhibiting HIV-RNA production, comprising contacting a cell population infected with HIV with a composition comprising a PEG-ASNase compound or asparaginase, and optionally at least one compound selected from the group consisting of protease inhibitor compounds, ribonucleotide reductase inhibitor compounds and HIV reverse transcriptase inhibitor compounds.

Another preferred embodiment according to the invention is a method of inhibiting HIV-RNA production, comprising contacting a cell population infected with HIV with a composition comprising a compound of formula I.

Another preferred embodiment according to the invention is a method of inhibiting HIV-RNA production, comprising contacting a cell population infected with HIV with a composition comprising MISID.

Another preferred embodiment according to the invention is a method of inhibiting HIV-RNA production, comprising contacting a cell population infected with HIV with a composition comprising a PEG-ASNase compound.

According to another preferred embodiment of the invention, the protease inhibitor compounds are selected from Saquinovir, Nelfinavir, Endinovere, Indinavir, Ritonavir, Crixivan, Viracept, Norvir, and VX-478.

According to a more preferred embodiment of the invention, the protease inhibitor compound is Saquinovir.

According to another preferred embodiment of the invention, the HIV reverse transcriptase inhibitor compounds are selected from AZT (Retrovir, zidovudine) ddI (Videx, didanosine) ddC (Hivid, zalcitabine), d4T (Zerit, stavudine) and 3TC (Epivir, lamivudine).

According to another preferred embodiment of the invention, the HIV reverse transcriptase inhibitor compound is AZT.

According to another preferred embodiment of the invention, the ribonucleotide reductase inhibitor compounds are selected from Hydroxyurea (HU), BW-348U87, 3-aminopyridine-2-carboxaldehyde thiosemicarbazone (3-AP) Amidox (VF 236; NSC-343341; N,3,4-trihydroxybenzenecarboximidamide), BILD 1257 (2-benzyl-3-phenylpropionyl-L-(N-methyl)valyl-L-3-(methyl)valyl-L-(N4,N4-tetramethylene)asparaginyl-L-(3,3-tetramethylene)aspartyl-L-(4-methyl)leucine), BILD 1357 (2-benzyl-3-phenylpropionyl-L-(N-methyl)valyl-L-3-(methyl)valyl-L-(N4,N4-tetramethylene)asparaginyl-L-(3,3-tetramethylene)aspartic acid 1-[1(R)-ethyl-2,2-dimethylpropylamide]), BILD 1633, BILD 733 (3-phenylpropionyl-L-(N-methyl)valyl-L-[3-methyl)valyl-L-[3-(pyrrolidin-1-ylcarbonyl)]alanyl-L-(1-carboxycyclopentyl)glycyl-L-(4-methyl)leucinol), BILD 1263 (2-benzyl-3-phenylpropionyl-L-(N-methyl)valyl-L-3-(methyl)valyl-L-(N4,N4-tetramethylene)asparaginyl-L-(3,3-tetramethylene)aspartyl-L-(4-methyl)leucinol), BILD1351 (1-[1(S)-[5(S)-[3-[(all-cis)-2,6- dimethylcyclohexyl]ureido]-2(S)-(3,3-dimethyl-2-oxobutyl)-6,6-dimethyl-4-oxoheptanoylamino]-1-[1(R)-ethyl-2,2-dimethylpropylcarbamol]methyl]cyclopentanecarboxylic acid]), CI-F-araA (2-chloro-9-(2-deoxy-2-fluoro-beta-D-arabinofuranosyl)adenine, DAH (D-aspartic-beta-hydroxamate), DDFC (2'-deoxy-2',2'-difluorocytidine),Didox (VF 147; NSC 324360; N,3,4-trihydroxybenzamide), Eurd (3'-Ethynyluridine),GTI 2040, GTI 2501,IMHAG (1-isoquinolylmethane-N-hydroxy-N'-aminoguanine), LY 207702 (2',2'-difluoro-2'-deoxyribofuranosyl-2,6-diaminopurine), LY 295501 (N-[[3, 4-dichlorophenyl)amino]carbonyl]2,3-dihydro-5-benzofuransulfonamide), MDL 101731 (FMdC; KW 2331; (2E)-2'-deoxy-2'-(fluoromethylene)cytidine), Parabactin, Sulofenur (LY 186641; N-[[(4-chlorophenyl)amino] carbonyl]-2,3-dihydro-1H-indene-5-sulfonamide), TAS 106 (Ecyd; 3'-ethynylcytidine),Triapine (OCX 191; OCX 0191), Trimidox (VF 233; N,3-4,5-tetrahydroxybenzene carboximidamide), and a compound of formula I.

According to another preferred embodiment of the invention, the ribonucleotide reductase inhibitor compound is the compound of formula I.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is lower alkyl, lower alkenyl, lower alkynyl, or an electron withdrawing group; and R2 is lower alkyl, lower alkenyl, lower alkynyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is lower alkyl, lower alkenyl, lower alkynyl, or a halogen group; and R2 is lower alkyl, lower alkenyl, lower alkynyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is lower alkyl or a halogen group; and R2 is lower alkyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is a halogen group; and R2 is lower alkyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is lower alkyl; and R2 is lower alkyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is a bromine or chlorine atom; and R2 is a methyl group or an isopropyl group; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is a methyl group; and R2 is lower alkyl; or a pharmaceutically acceptable salt thereof, an N-oxide thereof, a solvate thereof, an acid bioisostere thereof, or prodrug thereof.

According to another preferred embodiment of the invention, this invention is directed to a method of inhibiting or treating Human Immunodeficiency Virus (HIV) infection, comprising administering to a patient in need of such treatment a pharmaceutically effective amount of compound of formula I wherein R1 is a methyl group; and R2 is an isopropyl group; or a pharmaceutically acceptable salt thereof, an N-oxide thereof, a solvate thereof, an acid bioisostere thereof, or prodrug thereof.

According to another preferred embodiment of the invention, the protein synthesis inhibitor compound is PEG-ASNase.

According to another preferred embodiment of the invention, the protein synthesis inhibitor compound is asparaginase.

According to another preferred embodiment of the invention, the protease inhibitor compound is Saquinovir or Endinovere.

According to another preferred embodiment of the invention, the protease inhibitor compound is Saquinovir.

According to another preferred embodiment of the invention, the HIV reverse transcriptase inhibitor compounds are selected from AZT and 3-TC According to another preferred embodiment of the invention, the ribonucleotide reductase inhibitor compound is MISID (PL-7).

According to another preferred embodiment of the invention the compounds of use according to the invention are administered in concurrent combination.

According to another preferred embodiment of the invention the compounds of use according to the invention are administered sequentially.

According to another preferred embodiment of the invention the compounds of use according to the invention are administered sequentially, preferably by administering a protease inhibitor followed by the PEG-ASNase compound or asparaginase.

According to another preferred embodiment of the invention the compounds of use according to the invention are administered sequentially, preferably by administering Saquinavir followed by the PEG-ASNase compound or asparaginase.

According to another preferred embodiment of the invention the compounds of use according to the invention are administered sequentially, preferably administering in the order Saquinavir, followed by the PEG-ASNase compound or asparaginase, followed by one or more compounds selected from the group consisting of HIV reverse transcriptase inhibitor compounds and ribonucleotide reductase inhibitor compounds.

According to another preferred embodiment of the invention is a method of inhibiting or treating Human Immunodeficiency Virus (HIV) infection, comprising administering to a patient in need thereof a synergistic combination of a PEG-ASNase compound or asparaginase, and at least one compound selected from the group consisting of protease inhibitor compounds, ribonucleotide reductase inhibitor compounds and HIV reverse transcriptase inhibitor compounds.

According to another preferred embodiment of the invention is a method of inhibiting or treating Human Immunodeficiency Virus (HIV) infection, comprising administering to a patient in need thereof a synergistic combination of a PEG-ASNase compound and at least one protease inhibitor compound.

According to another preferred embodiment of the invention is a method of inhibiting or treating Human Immunodeficiency Virus (HIV) infection, comprising administering to a patient in need thereof a synergistic combination of a PEG-ASNase compound and at least one ribonucleotide reductase inhibitor compound.

According to another preferred embodiment of the invention is a method of inhibiting or treating Human Immunodeficiency Virus (HIV) infection, comprising administering to a patient in need thereof a synergistic combination of a PEG-ASNase compound and at least one HIV reverse transcriptase inhibitor compound.

According to another preferred embodiment of the invention is a method of inhibiting or treating Human Immunodeficiency Virus (HIV) infection, comprising administering to a patient in need thereof a synergistic combination of a PEG-ASNase compound and at least one protease inhibitor compound and at least one ribonucleotide reductase inhibitor compound.

According to another preferred embodiment of the invention is a method of inhibiting or treating Human Immunodeficiency Virus (HIV) infection, comprising administering to a patient in need thereof a synergistic combination of a PEG-ASNase compound and at least one protease inhibitor compound and at least one HIV reverse transcriptase inhibitor compound.

According to another preferred embodiment of the invention is a method of inhibiting or treating Human Immunodeficiency Virus (HIV) infection, comprising administering to a patient in need thereof a synergistic combination of a PEG-ASNase compound and at least ribonucleotide reductase inhibitor compound and at least HIV reverse transcriptase inhibitor compound.

It is a further object of the invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

Without being limited by theory, it is believed that the invention operates with the following mechanism. T-cells are the main cells in the mammalian body that are infected with HIV virus. T-cells are considered to be the viral factories for HIV infection. In order to re-infect new T-cells, the HIV virus must enter the T-cell and be able to replicate. The viral replication and encapsulation process requires the participation of intracellular enzymes. PEG-ASNase, a specific protein synthesis inhibitor compound to thymic-lineage cells, is shown to very useful in inhibiting synthesis of enzymes required for competent replication and assembly of the HIV virus and in providing other antiproliferative effects related to the HIV virus. Furthermore, a combination of PEG-ASNase or asparaginase, and one or more compounds selected from the group consisting of a protease inhibitor compound, a HIV-RT inhibitor compound, and a ribonucleotide reductase inhibitor compound, has a synergistic effect to reduce the viral burden for prolonged periods of time. The intracellular mechanism by which PEG-ASNase is believed to operate is to prevent a T-cell infected with HIV virus from synthesizing intracellular and viral proteins by adversely affecting the supply of the amino acid asparagine (Asn). Thus, by treating infected T-cells with an asparaginase such as PEG-ASNase, synthesis of cellular and viral proteins is inhibited. These proteins are necessary for the transcription and translation of the virally coded genes from the provirus, integrated viral origin DNA into mammalian DNA. Once viral-origin RNA is transcribed by RNA polymerases from the provirus, there are two pathways that may be followed. This RNA may be used by ribonucleotide s to produce viral-origin proteins, such as HIV-RT. Later, the same RNA may be processed by rev-protein into genomic HIV-1 RNA. This RNA will be attached to an already synthesized HIV-RT and when two such molecules are present together they constitute the genomic material of a new HIV virus is constituted. HIV proteases are involved in processing the viral origin proteins into the final viral packaging. The new HIV-1 virus may then bud off the T-cell as a new, complete virus. Thus, a protease inhibitor compound in combination with an asparaginase such as PEG-ASNase, can inhibit the processes required for HIV-1 viral replication in a synergistic manner.

The compositions and methods of therapy of the present invention are useful in the inhibition of HIV protease, the prevention or treatment of infection by HIV and the treatment of consequent pathological conditions such as AIDS. Treating AIDS or preventing or treating infection by HIV is defined by including but not limited to treating a wide range of states of HIV infection; AIDS, ARC (AIDS) related complex, both symptomatic and asymptomatic and actual or potential exposure to HIV. For example, the compounds of this invention are useful in treating infection by HIV after suspected past exposure to HIV by, for example, blood transfusion, exchange of body fluids, bites, accidental needle sticks, and exposure to patient blood during surgery.

In the treatment or prevention method according to the invention the PEG-ASNase compound or asparaginase, and optionally a compound selected from the group consisting of a protease inhibitor compound, a HIV reverse transcriptase inhibitor compound and a ribonucleotide reductase inhibitor compound, may be administered in different ways, such as in combination therapies optionally employing medical procedures. For example a PEG-ASNase compound and optionally one or more compounds selected from the group consisting of protease inhibitor compounds, HIV reverse transcriptase inhibitor compounds and ribonucleotide reductase inhibitor compounds, may be administered to a patient concomitantly or at different times provided that they are administered such that at some period of time there are pharmaceutically effective amounts of both compounds present in the patient such that a therapeutic effect according to the invention results.

Thus, it is a further object of the invention to provide a kit for treating or preventing a physiological condition associated with HIV, said kit comprising a plurality of separate containers, wherein at least one of said containers contains a PEG-ASNase compound or asparaginase, and at least another of said containers contains one or more compounds selected from the group consisting of protease inhibitor compounds, HIV reverse transcriptase inhibitor compounds and ribonucleotide reductase inhibitor compounds, and said containers optionally contain a pharmaceutical carrier, which kit may be effectively utilized for carrying out combination therapies according to the invention.

Thus, it is a further object of the invention to provide a pharmaceutical kit for treating or preventing a physiological condition associated with HIV, said kit comprising a plurality of separate containers, wherein at least one of said containers contains a compound of formula I and at least another of said containers contains one or more compounds selected from the group consisting of PEG-ASNase compounds, protease inhibitor compounds, HIV reverse transcriptase inhibitor compounds and ribonucleotide reductase inhibitor compounds, and said containers optionally contain a pharmaceutical carrier, which kit may be effectively utilized for carrying out combination therapies according to the invention.

A further embodiment for a kit would be wherein at least one of said containers should contain a PEG-ASNase compound without the presence of a protease inhibitor compound, a HIV reverse transcriptase inhibitor compound or a ribonucleotide reductase inhibitor compound, and at least another of said containers should contain one or more compounds selected from the group consisting of protease inhibitor compounds, HIV reverse transcriptase inhibitor compounds and ribonucleotide reductase inhibitor compounds, without the presence of a PEG-ASNase compound.

A further embodiment for a kit would be wherein at least one of said containers should contain a compound of formula I without the presence of a PEG-ASNase compound, a protease inhibitor compound, a HIV reverse transcriptase inhibitor compound or another ribonucleotide reductase inhibitor compound, and at least another of said containers should contain one or more compounds selected from the group consisting of protease inhibitor compounds, HIV reverse transcriptase inhibitor compounds and another ribonucleotide reductase inhibitor compound, without the presence the same compound of formula I.

A further embodiment for a kit would be wherein of said containers at least one of said containers should contain MISID (PL-7) without the presence of a PEG-ASNase compound, a protease inhibitor compound, a HIV reverse transcriptase inhibitor compound or another ribonucleotide reductase inhibitor compound, and at least another of said containers should contain one or more compounds selected from the group consisting of protease inhibitor compounds, HIV reverse transcriptase inhibitor compounds and ribonucleotide reductase inhibitor compounds, without the presence of MISID (PL-7).

It is to be understood that this invention covers all appropriate combinations of the particular and preferred groupings referred to herein.

Compounds according to the invention, for example, starting materials, intermediates or products, are prepared as described herein or by the application or adaptation of known methods, by which is meant methods used heretofore or described in the literature.

Compounds of Formula I may be prepared by the application or adaptation of known methods, by which is meant methods used heretofore or described in the literature. In particular, the known method of making derivatives of the formula I as described in Nandy P, Lien E J, Avramis V I, Med. Chem. Res. 1995, 5:664–679.

The compounds useful according to the invention optionally are supplied as salts. Those salts which are pharmaceutically acceptable are of particular interest since they are useful in administering the foregoing compounds for medical purposes. Salts which are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound useful according to the invention contains a carboxy group, or a sufficiently acidic bioisostere, base addition salts may be formed and are simply a more convenient form for use; and in practice, use of the salt form inherently amounts to use of the free acid form.

Also, where the compound useful according to the invention contains a basic group, or a sufficiently basic bioisostere, acid addition salts may be formed and are simply a more convenient form for use; and in practice, use of the salt form inherently amounts to use of the free base form.

The foregoing compounds useful according to the invention may also be mixed another therapeutic compound to form pharmaceutical compositions (with or without diluent or carrier) which, when administered, provide simultaneous administration of a combination of active ingredients resulting in the combination therapy of the invention.

While it is possible for the compounds useful according to the invention to be administered alone it is preferably to present them as pharmaceutical compositions. The pharmaceutical compositions, both for veterinary and for human use, useful according to the present invention comprise at lease one compound of the invention, as above defined, together with one or more acceptable carriers therefor and optionally other therapeutic ingredients.

In certain preferred embodiments, active ingredients necessary in combination therapy may be combined in a single pharmaceutical composition for simultaneous administration.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The oily phase of the emulsions of this invention may be constituted from known ingredients in a known manner. While the oily phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the emulsifying wax, and the way together with the oil and fat make up the emulsifying ointment base which forms the oily dispersed phase of a cream formulation. Emulgents and emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogue.

The choice of suitable oils or fats for the formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Solid compositions of may also be employed as fillers in soft and hard-filled gelatin capsules using such excipients as lactose or milk sugar as well as high molecular weight polyethylene glycols, and the like.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g. poly(d,1-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds useful according to this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The amount of each component administered is determined by the attending clinicians taking into consideration the etiology and severity of the disease, the patient's condition and age, the potency of each component and other factors.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The compounds of the invention, their methods or preparation and their biological activity will appear more clearly from the examination of the following examples which are presented as an illustration only and are not to be considered as limiting the invention in its scope.

Procedures for evaluating the biological activity of compounds or compositions according to the invention are carried out as described herein or by the application or adaptation of known procedures, by which is meant procedures used heretofore or as described in the literature.

EXPERIMENTAL

General Methodology for the MV-Reverse Transcriptase Assay, Non Radioactive (Boehringer Mannheim)

The following is a general procedure for the HIV-reverse transcriptase assay:

Day One
  Samples are supernatants and pellets obtained from the viral±drug flasks (incubation for seven days). They are not heat inactivated.
  Centrifuge the samples at 2000 g for 30 minutes at 4° C. Use 2500 rpm to achieve 2000 g.
  Transfer the supernatant to a sterile labeled tube.
  Add 0.5 ml peg solution
    Use 1.2 m nacl as the diluent for peg.
    Peg solution: 30% w/v, 30 g in 100 ml.
  Mix thoroughly
  Incubate o/n at 0° C. (on ice in the refrigerator)
Day Two
  Centrifuge 500 μl of the samples at 8000 g for 10 minutes at 4° C. Use 8000 rpm to achieve 8000 g.
  Discard the supernatant. Be careful to remove all drops of peg from the samples.
  Add 40 μl lysis buffer solution
  Re-suspend pellet completely.
  Transfer the suspension to a fresh reaction tube.
  Incubate at rt (25° C.) for 30 minutes
  Make the standard dilutions:

| STEP | HIV-1-RT | LYSIS BUFFER | HIV-1-RT CONC. (Ng/Well) |
|---|---|---|---|
| 0 | 0 | 150 Ml | 0 |
| 1 | 10 μL (SOLUTION 1) | 390 Ml | 2.0 |
| 2 | 150 μL OF STEP 1 | 150 Ml | 1.0 |
| 3 | 150 μL OF STEP 2 | 150 Ml | 0.5 |
| 4 | 150 μL OF STEP 3 | 150 Ml | 0.25 |
| 5 | 150 μL OF STEP 4 | 150 Ml | 0.125 |
| 6 | 150 μL OF STEP 5 | 150 Ml | 0.0625 |

Transfer 40 μl of the standards to reaction tubes (n=7×2).
  Make reaction buffer solution:
    reconstitute the template (vial 4) in 430 μl autoclaved water.
    add 1 ml incubation buffer per vial of nucleotides (vial 3).
    add 100 μl of the reconstituted template (vial 4) to the nucleotide solution vial (vial 3).
  Add 20 μl reaction buffer to all tubes, unknowns and standards.
  Incubate for up to 15 hours at 37° C. in a rack in the incubator.
Day Three
  Create a template for the Elisa assay using wordperfect;
  Open the foil packets and construct a mtp (microtiter plate) module using the frame and the strips provided in the kit.
  Unknown n=therefore, total specimens n=Standard n=
  Strips have 8 wells each, therefore need___$_{l\ strips}$
  Note: you have to round up to the closest multiple of 8.
  Transfer 60 μl from the reaction tubes to the corresponding wells of the mtp module as per template.
  Cover the mtp with the cover strip provided.
  Incubate at 37° C. in the incubator for 1 hour.
  If necessary, make the washing solution:
    Note: solution provided is a 10× solution, therefore it must be diluted using autoclaved water.
    Make 1 bottle wash solution by adding 225 ml autoclaved water to the bottle provided. Mix well. Keep on ice during the assay.
  Remove the solution completely by decanting.
  Wash the plate 5× using 250 μl per rinse with a 30 second soak time before decanting.
  Make the anti-dig-pod working solution
    Make the anti-dig-pod solution
      Add 500 μl autoclaved water to the anti-dig-pod vial (vial #6) store at 4° C., do not freeze
    Make the anti-dig-pod working solution
      Calculate the necessary volume:
      __wells×200 μl=__ml
      Use 50 μl anti-dig-pod solution (vial #6) for each 4.95 ml conjugate dilution buffer (solution #8).
      Add__ml anti-dig-pod solution (vial #6)
      To$_{13}$ ml conjugate dilution buffer (solution #8)
  Add 200 μl anti-dig-pod working solution per well of the mtp.
  Cover the mtp with the cover strip provided.
  Incubate at 37° C. in the incubator for 1 hour.
  Remove the solution completely by decanting.
  Wash the plate 5× using 250 μl per rinse with a 30 second soak time before decanting.
  Make the abts substrate solution with enhancer
    Make the abts substrate solution
      Dissolve the abts powder mixture (vial #10) in the bottle of substrate buffer (bottle #9).
      Calculate the necessary volume:
      __wells×200 μl=__ml
    Add the appropriate amount of enhancer to the solution. Use 1 mg substrate enhancer (vial #11) for each 1 ml abts substrate solution (bottle #9).
      Add__mg substrate enhancer (vial #11)
      To__ml abts substrate solution (bottle #9)
  Add 200 μl abts substrate solution with enhancer per well of the mtp.
  Read the plate at 405 nm (reference wavelength 490 nm) at 10, 20, and 30 minutes.

Example 1

Combination regimen of PEG-ASNase Compound and Saquinavir

Materials and Methods

The cell line used for these studies is CCRF/CEM/O, a human T-leukemic cell line. PEG-ASNase (ONCASPAR) is provided by Rhone-Poulenc Rorer. Saquinavir is commercially available. RPMI-1640 media (Irvine Scientific, Irvine, Calif.) is enriched with 10% Fetal Calf Serum (Gemini Biosource, Calabasas, Calif.), 5% 1M Hepes Buffer solution and 5% Non-essential amino acids (Irvine Scientific, Irvine, Calif.). The drug concentrations used are as follows:

PEG-ASNase IC50 alone: 0.4 IU/ml

Saquinavir IC50 alone: 25 $\mu$M

PEG/SAQ combo IC50:0.233 IU/ml+15.52 $\mu$M

Briefly, 2×10$^6$ cells/ml are stimulated with PHA+ media for 48 hours at 37° C. with 5% $CO_2$. Also, the same number of cells are incubated in PHA(phytohemagglutinin) free media for 48 hours to serve as the negative control. At this point the cells are inoculated with the HIV-1 virus as per standard protocol. PEG-ASNase and/or Saquinavir are added to the cells in the appropriate concentrations (see above). The control cells are resuspended in drug-free media for the duration of the exposure which lasted seven days. At day five, two 1 ml aliquots of media are removed from the flasks and stored under liquid nitrogen. At day seven, two more 1 ml aliquots of media are removed from the flasks and stored under liquid nitrogen. In addition, the remaining cells are pelleted and stored at −80° C.

The samples produced from this experiment are itemized and then assayed for HIV-RT using the Reverse Transcriptase Assay, non-radioactive (Boehringer Mannheim). The standard curve is determined and the HIV-RT levels for the experimental samples are calculated.

Results

The primary observation from the HIV-RT assays in these specimens from T-cells is that there is no HIV-RT/virus in the supernatant of the CEM/0 T-cells post treatment. The results of this experiment are illustrated in FIG. 1.

The T-cell pellets themselves are then examined for intracellular HIV-RT. PEG-ASNase at 0.4 IU/ml (approximate $IC_{50}$ concentration) demonstrated about 30% inhibition of HIV-RT. Saquinavir, the HMV protease inhibitor compound, alone at 25 $\mu$M (approximate $IC_{50}$ concentration) depleted HIV-RT activity by about 70% as compared to untreated control cell cultures HIV-RT. Lastly, we have shown that the concurrent combination of PEG-ASNase and Saquinavir are synergistic, thus the $IC_{50}$ concentrations of these drugs in combination are 0.233 IU/ml and 14.5 $\mu$M, respectively. These concentrations are much lower than their respective $IC_{50}$ values in CEM/0 T-cells. The combination regimen of PEG-ASNase and Saquinavir inhibited HIV-RT intracellularly by about 82.3% as compared to untreated control values.

Discussion

Since the T-cells did not shed HIV-1 in the supernatant after these drug treatments, it appears that PEG-ASNase and Saquinavir are not only synergistic against T-cells, but also are selectively synergistic against HIV-1. These drugs are sufficiently suppressive in releasing new HIV-1 particles to the media (equivalent serum or plasma of patients). The fact that the lower concentrations of the combination are more suppressive of HIV-RT than the most active of the two drugs Saquinavir at a higher concentration, strongly suggests that the combination is selectively inhibiting HIV at the provirus level.

Because these drugs and their combination suppress/inhibit HIV-RT intracellularly, it suggests that they inhibit HIV-1 at the provirus level. In other words, the integrated HIV provirus is producing mRNA, which is not translated into viral proteins and hence, the inhibition of the production of RT or complete virus particles to be shed in the media. Thus, on a theoretical basis, no further HIV-1 infection could be achieved of uninfected T-cells.

Experiment 2

Determination of Cytotoxicity

Materials and Methods

A human leukemic T-cell line, hereafter referred to as CEM/0 is used for this experiment. PEG-ASNase is obtained from Rhone-Poulenc Rorer Pharmaceuticals Inc under the tradename Oncaspar®. Saquinavir is obtained from Roche Laboratories under the tradename Invirase™. RPMI-1640 media obtained from Irvine Scientific, Irvine Calif. is enriched with 10% Fetal Calf Serum obtained from Gemini Biosource, Calabasas, Calif., 5% 1M Hepes buffer solution and 5% non-essential amino acids obtained from Irvine Scientific, Irvine Calif.

An experiment is carried out to determine the cytotoxicity of Saquinavir and PEG-ASNase. For determining the cytotoxicity of either compound alone, 2×10$^5$ cells/ml are incubated in 24-well plates with the following drug concentrations:

PEG-ASNase: 1.0, 0.75, 0.5, 0.4, 0.3, 0.2, 0.1, 0.03 IU/ml

Saquinavir: $10^{-4}$, $10^{-5}$, $10^{-6}$, $10^{-7}$, and $10^{-8}$ M

Results

The PEG-ASNase concentration that produces a cytostatic condition in CEM/0 cells in vitro is approximately 0.5 IU/ml. PEG-ASNase concentrations of 1 and 0.75 IU/ml produced significant cell kill and are cytotoxic to CEM/0 cells by 72 hours. The concentrations of 0.03, 0.1, 0.2, 0.3 and 0.4 IU/ml are marginally effective in preventing cell growth as compared to the control (untreated cells) growth rate. The cells treated with 0.5 IU/ml PEG-ASNase, however, showed a relatively flat cell growth line. Thus, a cytostatic effect is produced with this concentration over 72 hours. Therefore, a range of PEG-ASNase concentrations including 0.5 IU/ml are used in the combination regimen investigations. A drug, concentration and time dependent cytotoxic effect of PEG-ASNase in this T-cell line is shown.

Figure 2:
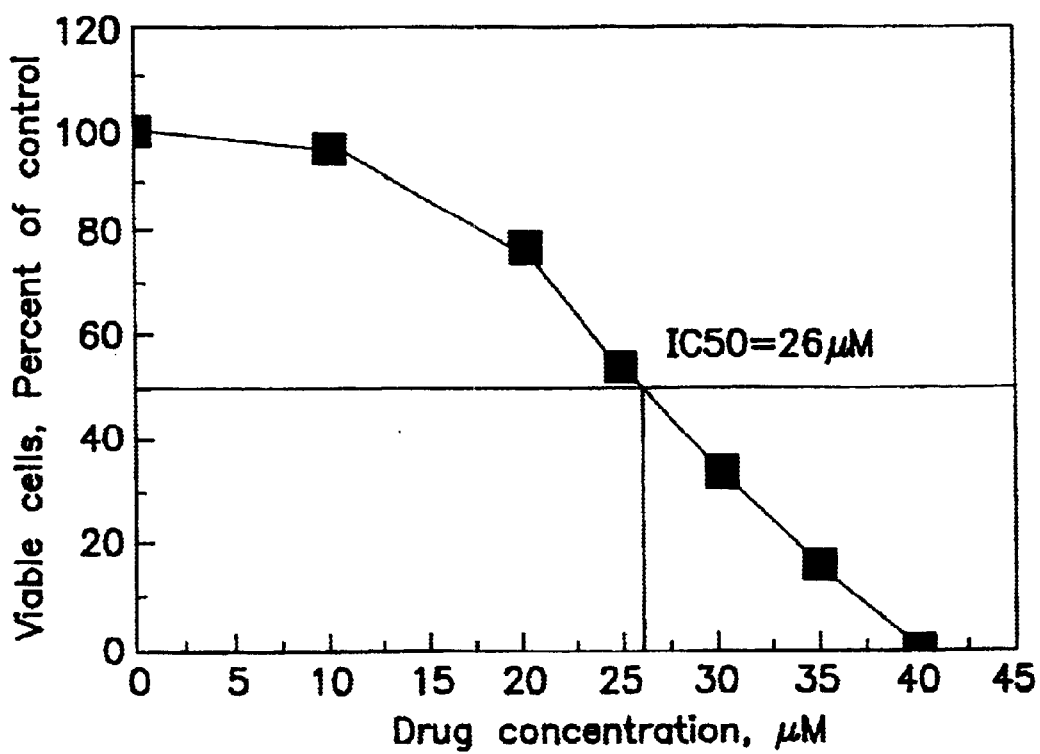
FIG. 2 represents T-Cell (CEM/0) cytotoxicity of Saquinavir, after 72 hours, for different drug concentrations.

The $IC_{50}$ of Saquinavir in CEM/0 cells is determined to be 26 $\mu$M after a 72 hour incubation period. The results are illustrated in FIG. 2. Multiple independent experiments with Saquinavir showed an $IC_{50}$ from 21–28 $\mu$M. Concentrations from 0.001 to 1 $\mu$M Saquinavir produced no cell kill. Concentrations of 10 $\mu$M produced only an 8.76% kill compared to untreated control samples. The highest concentration tested, 100 $\mu$M, killed 99.50% of the cells compared to control cells. Thus, a range of concentrations of 1 to 40 $\mu$M Saquinavir is used in subsequent experiments to investigate the combination Saquinavir/PEG-ASNase therapy in CEM/0 cells.

Experiment 3

Initial Sequential Combination Studies of Saquinavir and PEG-ASNase

Materials and Methods

Figure 3:
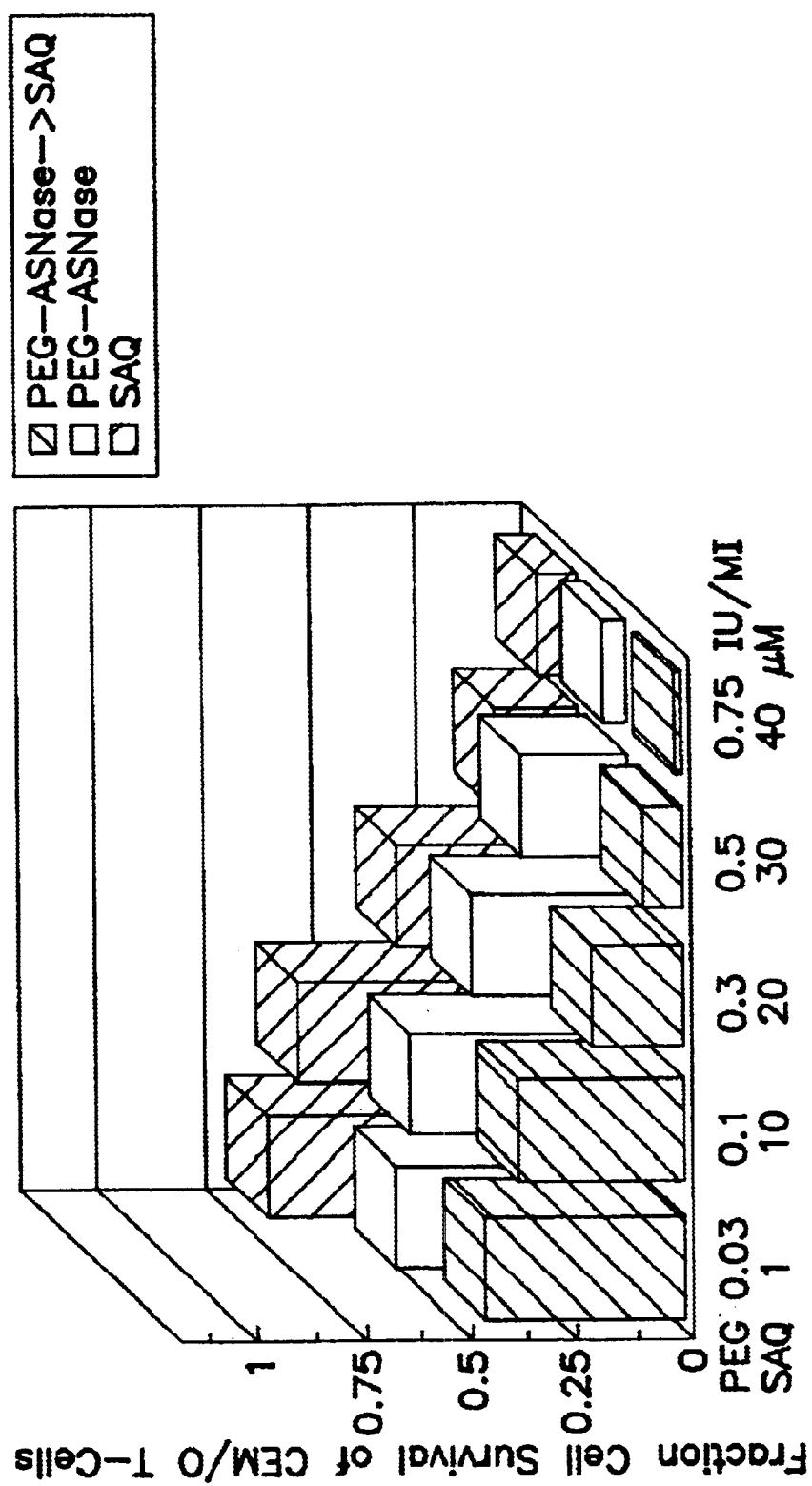
FIG. 3 represents T-Cell cytotoxicity of PEG-ASNase and Saquinavir alone, and in sequential combination (PEG-ASNase followed by Saquinavir), for different drug concentrations.

In this experiment, the described range of concentrations is used to investigate the combined regimen of Saquinavir and PEG-ASNase. For the sequential combination studies of PEG-ASNase followed by Saquinavir, cells are incubated with the concentrations provided below of PEG-ASNase for 24 hours. Then Saquinavir, in the concentrations provided below, is added to the appropriate cells for an additional twenty-four (24) hours, bringing the total exposure time to forty-eight (48) hours. The exposure involved 2×10$^5$ cells/ml being incubated in a tissue culture flask with concentrations of the drugs investigated as provided below. The results are illustrated in FIG. 3. The drug concentrations used are as follows:

PEG-ASNase: 1.020, 0.765, 0.510, 0.255 and 0.0255 IU/ml

Saquinavir: 40, 30, 20, 10 and 1 µM

In all in vitro studies, the negative control cells are incubated in a drug-free media for the same duration and under the same conditions as the experimental samples. Cell density is measured via cell counting using a Coulter Counter coupled with a Coulter Channelyzer for each of the experimental flasks at 24, 48 and 72 hours after incubation. Additionally, Trypan Blue Exclusion tests are performed for each of these experimental conditions. Cell numbers are corrected for the viability determined by the Trypan Blue test and presented as a percentage of the untreated control.

Figure 4:
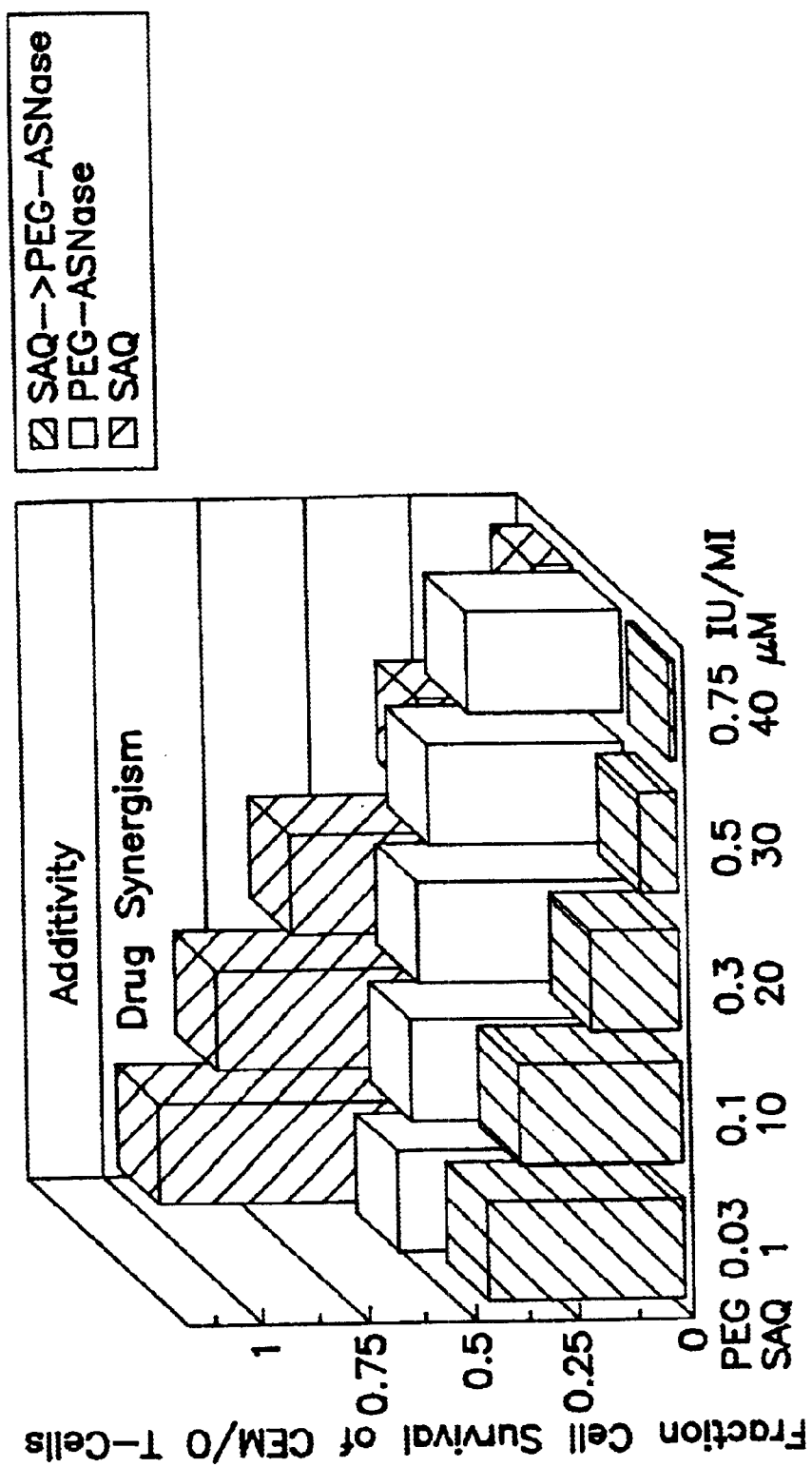
FIG. 4 represents T-Cell cytotoxicity of PEG-ASNase and Saquinavir alone, and in sequential combination (Saquinavir followed by PEG-ASNase), for different drug concentrations.
Figure 5:
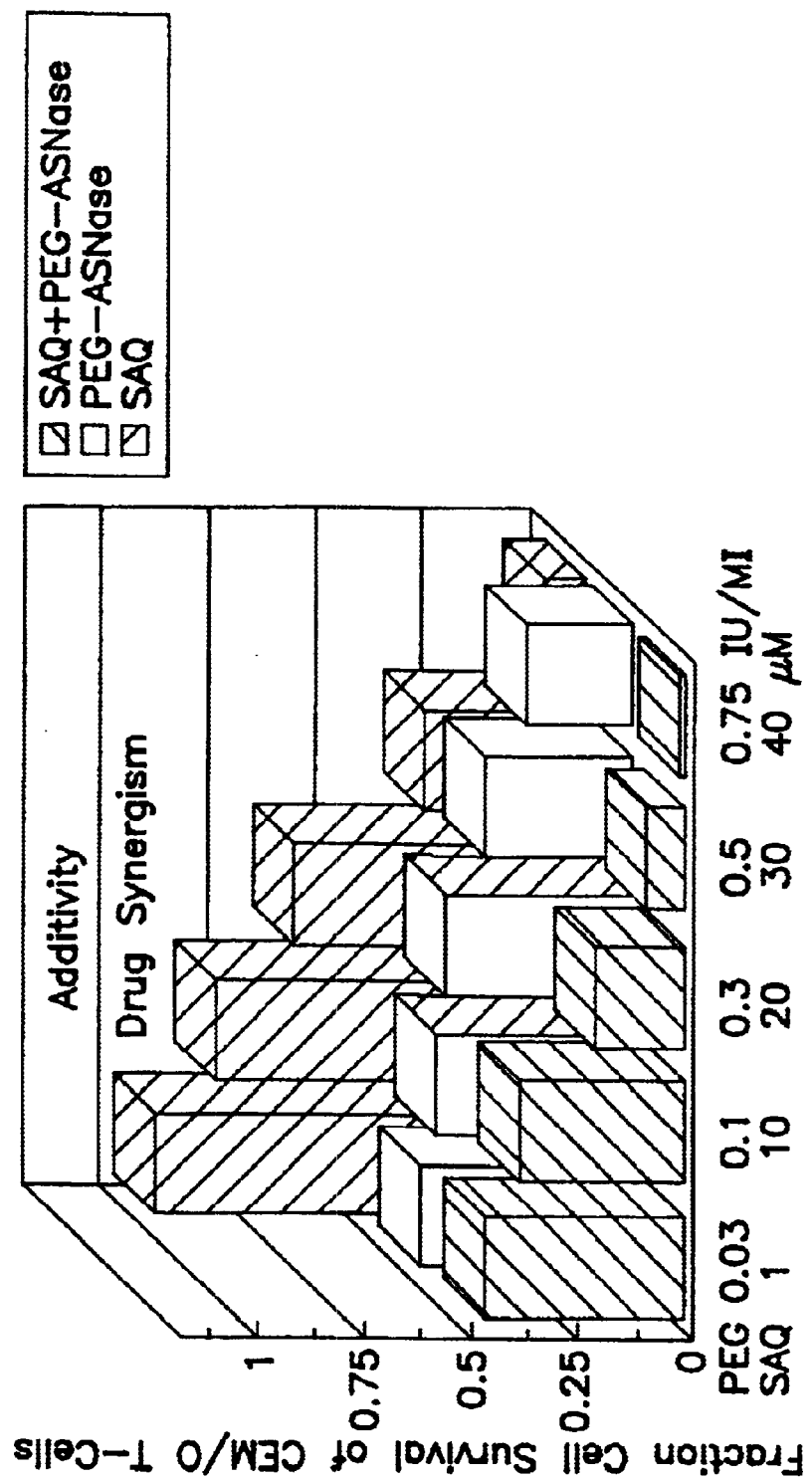
FIG. 5 represents T-Cell cytotoxicity of PEG-ASNase and Saquinavir alone, and in concurrent combination, for different drug concentrations.
Figure 6:
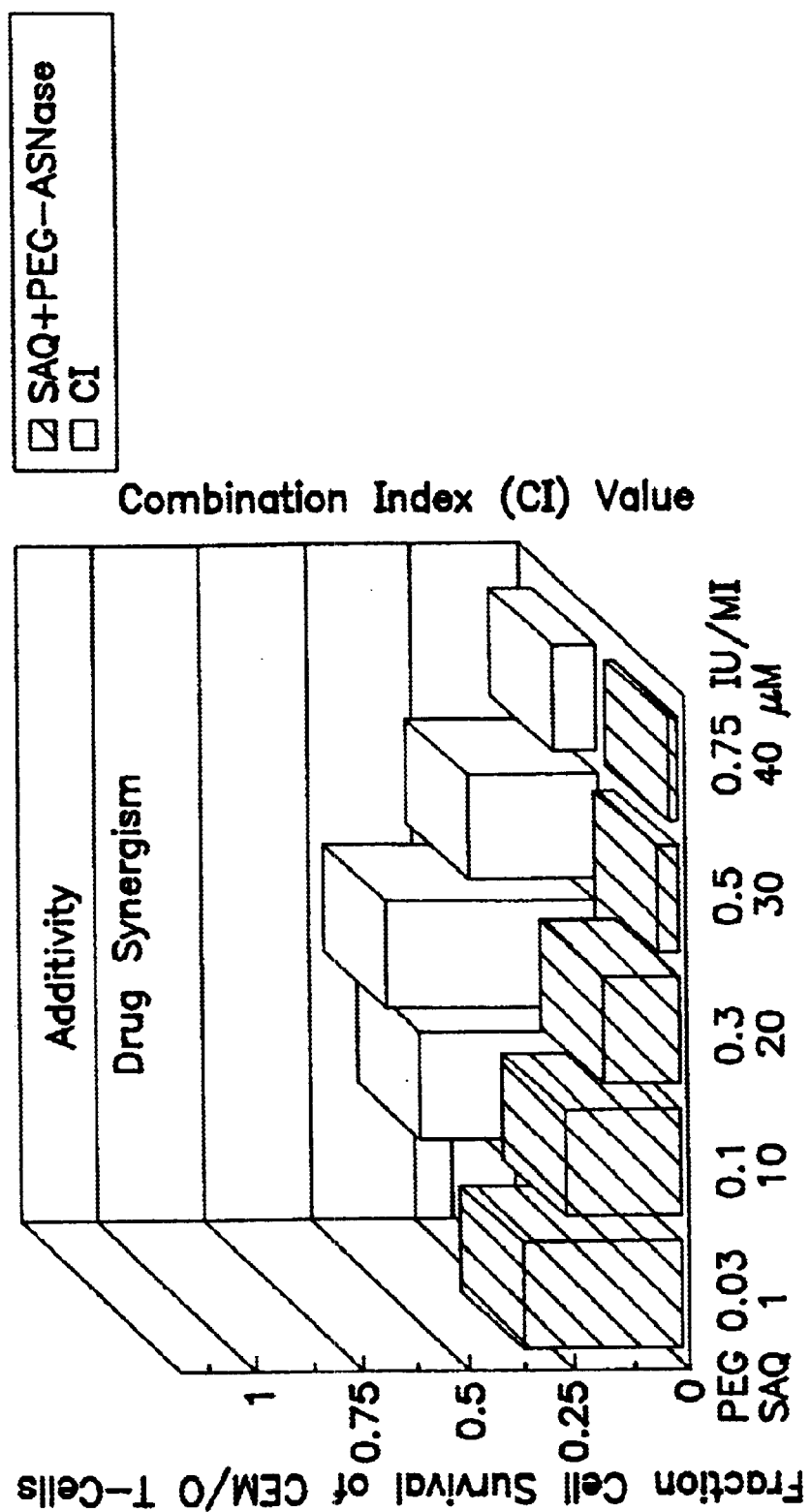
FIG. 6 represents T-Cell synergism of PEG-ASNase and Saquinavir in concurrent combination for different drug concentrations.
Figure 7:
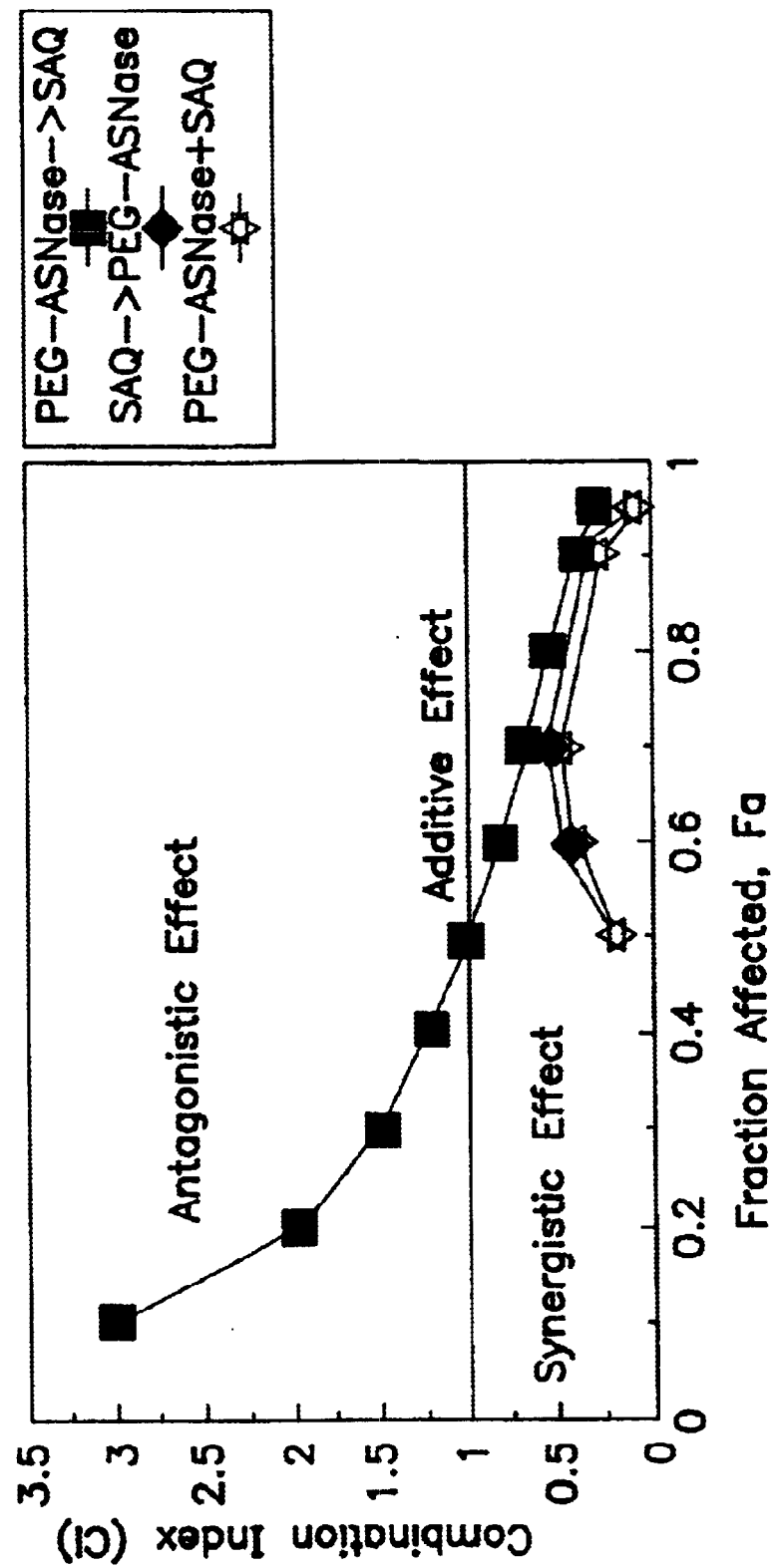
FIG. 7 represents the combination index (CI) in CEM/0 of sequential combination of Saquinavir followed by PEG-ASNase, and sequential combination of PEG-ASNase followed by Saquinavir, and concurrent combination of PEG-ASNase and Saquinavir.

The reverse sequence is also tested. The results are illustrated in FIG. 4. Saquinavir is administered and the cells incubated for twenty-four (24) hours followed by addition of PEG-ASNase and an additional incubation period of twenty-four (24) hours, bringing the total exposure time to forty-eight (48) hours. Other than the drug sequence, the methodology is the same as that mentioned immediately above. The concurrent combination regimen is also tested using the same methodology. The results are illustrated in FIGS. 5, 6, and 7. The concurrent combined methodology experiment had the samples exposed to forty-eight (48) hours of concurrent combined exposure.

Results

Each regimen tested showed synergistic effects at certain ranges tested. The sequential combined regimen of PEG-ASNase followed by Saquinavir showed a 1.72-fold synergy after forty-eight hour exposure. This is similar to the synergies shown from the other sequential regiment and the concurrent regimen. The invention shows the very desirable result of producing optimal synergism at a level that allows for some cell survival.

Experiment 4

Determination of Amino Acid Levels

Materials and Methods

Experiments to determine the amino acid level in cell suspensions and cell media are performed to determine the effect of PEG-ASNase on the amino acid levels, particularly the levels of asparagine, glutamine, and aspartic acid.

Samples of 50 µl media and 10 µl of 1 mM aminoadopic acid are added to 450 µl of cold methanol in 1.5 ml microfuge tubes. The mixtures are vortexed and centrifuged at 8700 g for two minutes. The supernatants are transferred to borosilicate glass test tubes (13×100 mm) and lyophilized. The specimens are stored at −20° C. until they are analyzed by HPLC. Prior to HPLC analysis, the samples are dissolved in a buffer containing 95% 7 nM disodium hydrogen phosphate and 5% acetonitrile.

Results

Figure 8:
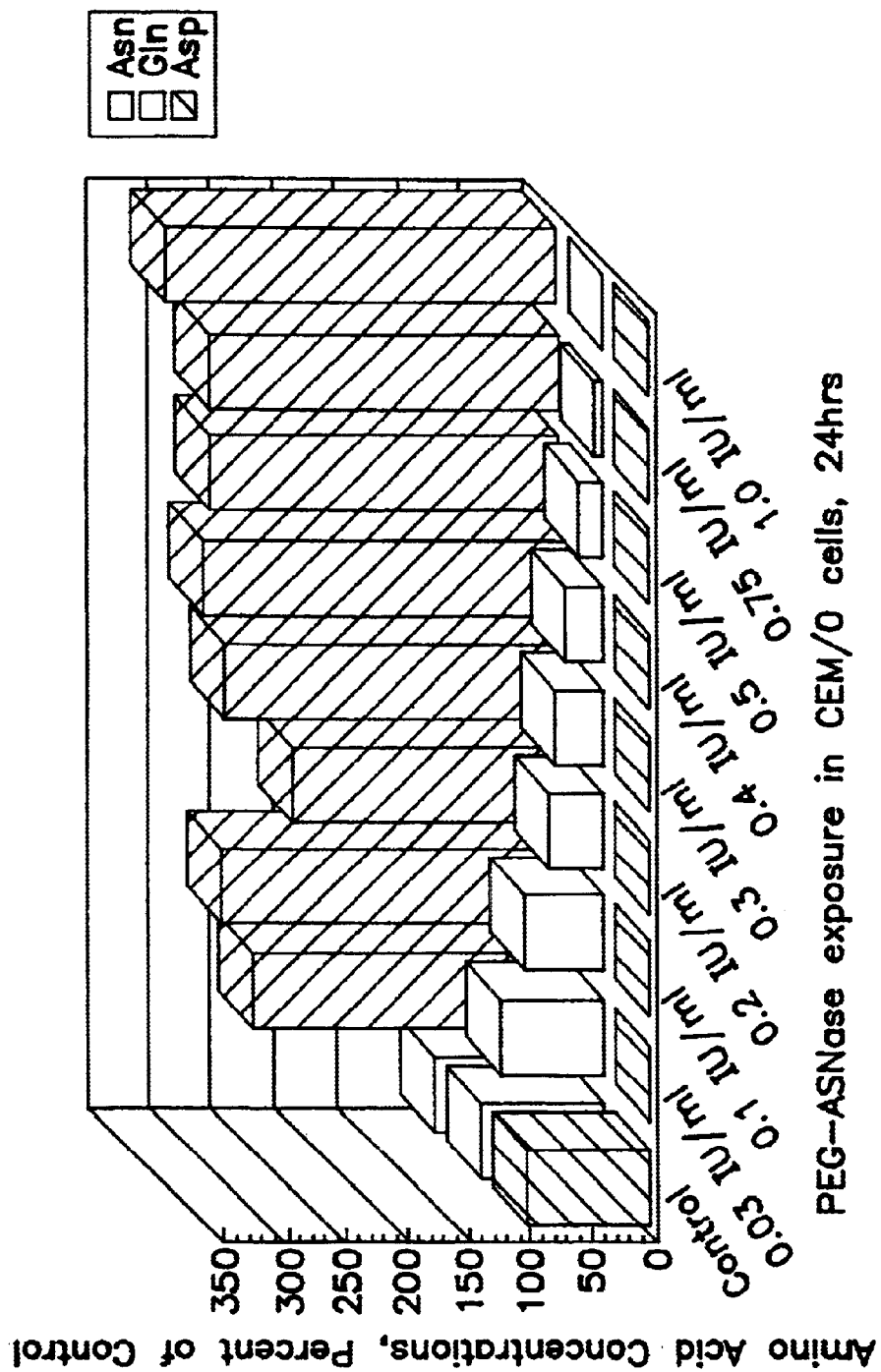
FIG. 8 represents the depletion of Asparagine, Glutamine and Aspartic acid concentrations in CEM/0 T-cells after exposure to different concentrations of PEG-ASNase for 24 hours.
Figure 8A:
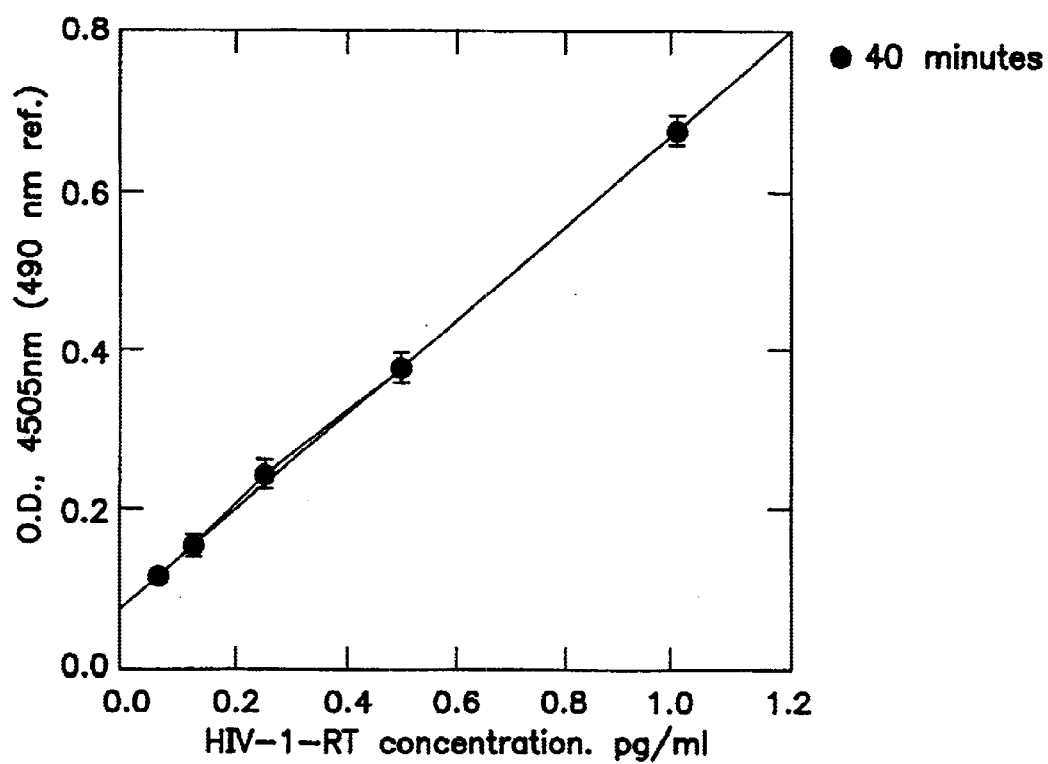
FIG. 8a represents a calibration curve of the optical density (OD) of different concentrations of HIV-1 RT.

After twenty-four hours exposure of CEM/0 cells to various concentrations of PEG-ASNase, a significant depletion of asparagine (Asn) is observed. The asparagine level is less than 3.0% of the untreated control. Also, a dose dependent depletion of glutamine (gln) to levels that are less than 3.0% of the untreated control are observed in the experiment using the highest PEG-ASNase concentration. The aspartic acid (Asp) levels are elevated in comparison to the untreated control to levels representing a 200 to 300% increase. The results are illustrated in FIG. 8. The calibration curve used to calculate the amount of HIV-RT is illustrated in FIG. 8a.

Even at the lowest levels of PEG-ASNase tested, a depletion of Asn after twenty-four hours is seen. This is consistent with PEG-ASNase being able to kill illicit T-cells by depletion of vital amino acids, particularly asparagine. PEG-ASNase also depletes Gln levels that may be important in the mechanism of destroying T-cells.

Experiment 5

Determination of the Effect of the Exposure of HIV-RNA in T-cell Pellets to a Combination of PEG-ASNase and Saguinavir This experiment is carried out using a similar procedure, and the same concentrations of materials as in Experiment 1, however the exposure of HIV-RNA in T-cell pellets to a combination of PEG-ASNase and Saquinavir is measured. The results of this experiment are shown in Tables 1 and 2 and in graphs 9 and 9a. It should be noted that "PEG" in Table 2 represents PEG-ASNase.

Figure 9:
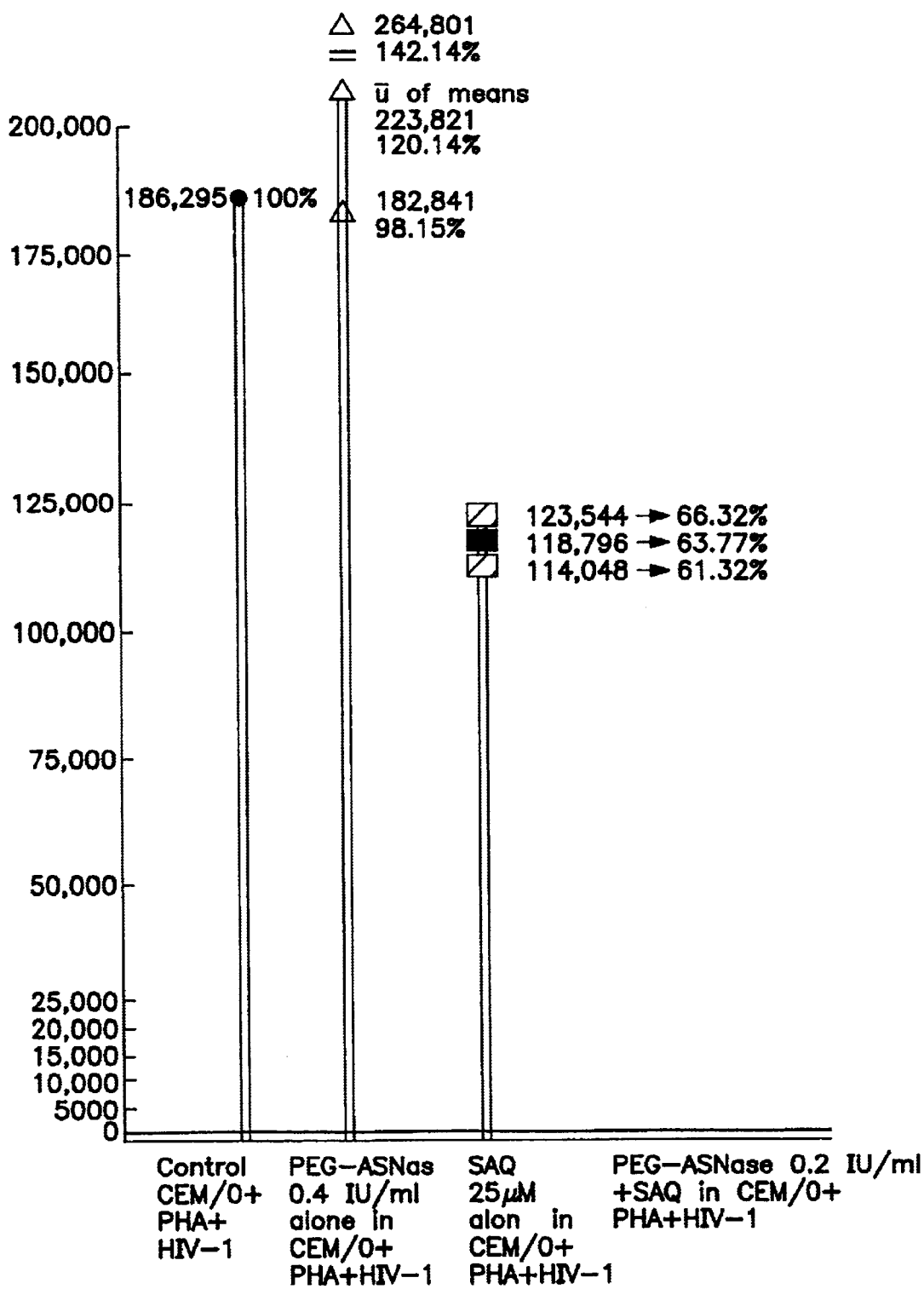
FIG. 9 represents the number of HIV RNA copies per cell pellets after exposure of the cells to PEG-ASNase and Saquinavir alone and in combination.
Figure 9A:
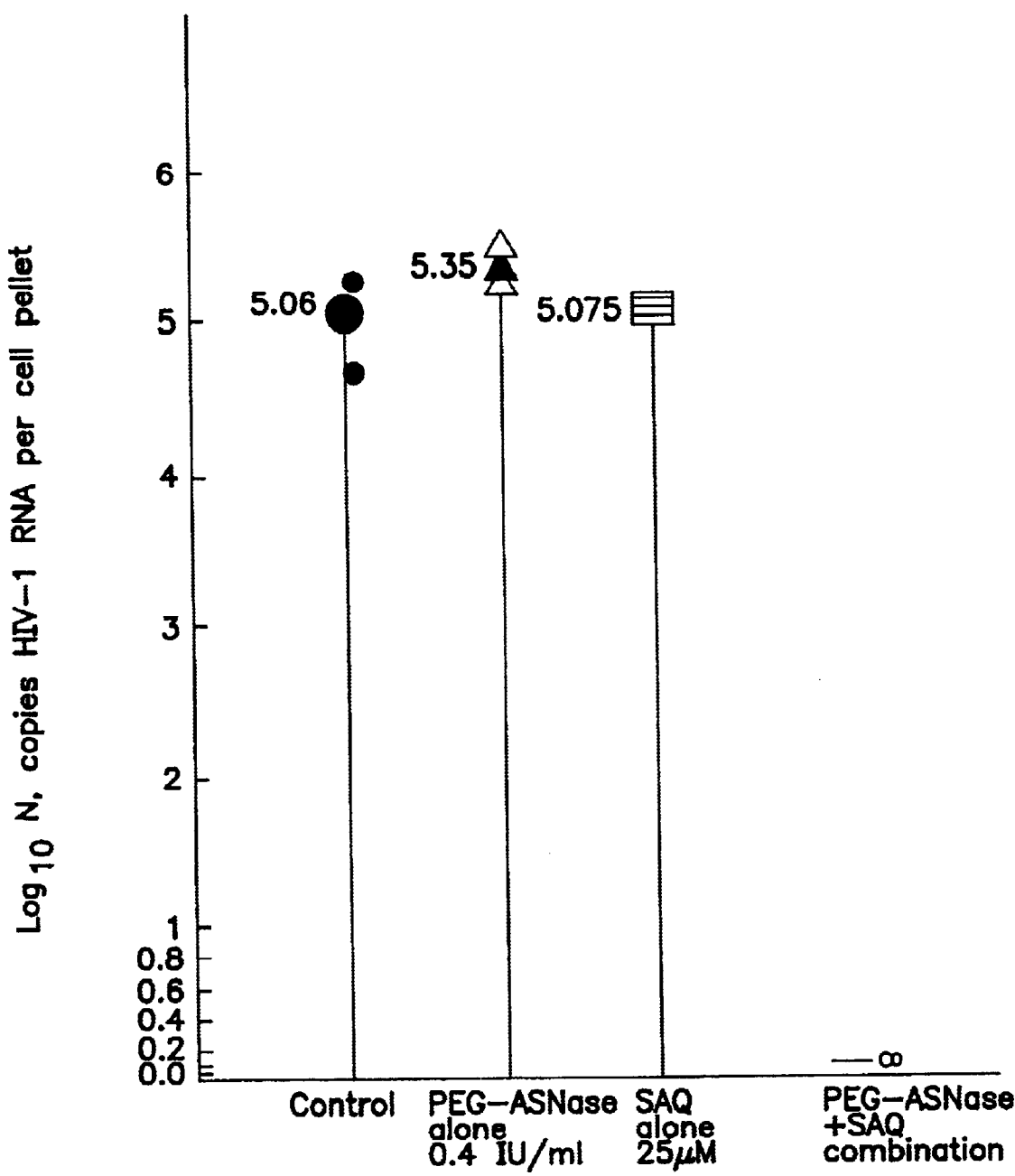
FIG. 9a represents $Log_{10}$ of the number of HIV RNA copies per cell pellets after exposure of the cells to PEG-ASNase and Saquinavir alone and in combination.

These results show that PEG-ASNase had no apparent effect on RNA production of HIV-1, whereas it had a moderate effect in inhibiting HIV-RT in the same cell culture by day 7 (see experiment 5a). Thus PEG-ASNase is inhibiting protein biosynthesis even at the HIV-RT level (see experiment 5a). Saquinavir alone has an inhibitory effect on HIV-1 RNA production, inhibiting approximately 36% in comparison with the control (FIGS. 9 and 9a). The combination of PEG-ASNase and Saquinavir, at synergistically reduced concentrations, resulted in inhibiting approximately 12% of HIV-RT (see experiment 5a). Yet, in the same cultures, the combination of PEG-ASNase and Saquinavir, at the reduced concentrations, yielded no detectable HIV-1 RNA up to the lower limits of the assay of 400 copies of RNA per pellet. This data demonstrates that the protein inhibitor (PEG-ASNase) plus the HIV-1 protease inhibitor (Saquinavir) act not only synergistically but selectively against HIV-RT and more importantly selectively against HIV-1 RNA production.

Experiment 5a

Determination of the Effect of PEG-ASNase±Saguinavir on the HIV RT Levels of HIV-1 Infected Cell Pellets This experiment is carried out using a similar procedure, and the same concentrations of materials as in Experiment 7, however the exposure of the HIV virus in T-cell pellets to PEG-ASNase and Saquinavir alone, and in combination is measured. The results of this experiment are shown in Table 2a. It should be noted that "PEG" in Table 2a represents PEG-ASNase.

These results show that PEG-ASNase had a moderate effect in inhibiting HIV-RT. Thus PEG-ASNase is inhibiting protein biosynthesis even at the HIV-RT level. Saquinavir alone also has an inhibitory effect on HIV-1 RT, inhibiting approximately 15% in comparison with the. The combination of PEG-ASNase and Saquinavir, at synergistically reduced concentrations, resulted in inhibiting approximately 12% of HIV-RT.

Experiment 6

Determination of the Inhibition of HIV-RNA in Supernatant of CEM/0 T-Cells by a Combination Regimen of PEG-ASNase and Saguinavir Experiment 5 illustrates the results of the exposure of HIV-RNA in T-cell pellets to a combination of PEG-ASNase and Saquinavir. However, the experimental procedure did not remove the HIV-1 particle from the supernatant to simulate the continuous exposure of the T-cells to HIV-1 virus. Thus, there is always HIV-1 virus in the supernatant of the T-cell cultures.

It is discovered that the combination of PEG-ASNase and Saquinavir inhibited the HIV-RNA in the cells pellets to a significant degree, and, in some wells, the HIV-RNA could not be quantitated after treatments with the PEG+SAQ drug combination, thus, we had achieved complete inhibition of HIV-RNA.

The supernatants of the T-cells from experiment 5 are analyzed for HIV-RNA and the results are shown in Tables 3 and 4. It should be noted that "PEG" in Table 3 represents PEG-ASNase. PEG alone inhibited HIV-RNA in the supernatants by approximately 60% and SAQ approximately by 68%. The combination of PEG+SAQ reduced the HIV-RNA by approximately 75% in the supernatant in comparison to untreated control. This RNA inhibition pattern fits nicely with the ones indicated in the earlier experiments reporting inhibiting HIV-RT and HIV-RNA from the same experiment.

Since these drugs do not "kill" the HIV virus in the supernatant, the reduction of the HIV-RNA can only be achieved by the "loss" due to infection and non-regeneration, via replication, due to the inhibition of the virus replication cycle by these drugs, specifically no HIV-RNA is produced intracellularly to be exported into the media as such or as complete HIV-virus particles.

Experiment 7

Determination of the Effect of PEG-ASNase±Saguinavir±AZT±MISID (PL-7) on the HIV RT Levels of HIV-1 Infected Cell Pellets Materials and Methods: The cell line used for this experiment is CEM/0, a human T-cell leukemic cell line. PEG-ASNase (ONCASPAR) is provided by Rhone-Poulenc Rorer. Saquinavir is commercially available. AZT is purchased from Sigma. MISID, a ribonucleotide reductase inhibitor, is synthesized described in Nandy P, Lien E J, Avramis V I, Med. Chem. Res. 1995, 5:664–679. RPMI-1640 media (Irvine Scientific, Irvine, Calif.), is enriched with 10% Fetal Calf Serum (Gemini Biosource, Calabasas, Calif.), 5% 1M Hepes Buffer solution and 5% Non-essential amino acids (Irvine Scientific, Irvine, Calif.). The drug concentrations used are as follows:

| | |
|---|---|
| PEG-ASNase IC50 alone: | 0.40 IU/ml |
| Saquinavir IC50 alone: | 25 $\mu$M |
| AZT | 1 $\mu$M |
| MISID (PL-7) | 0.685 $\mu$M |
| PEG IC50 combination: | 0.23 IU/ml |
| SAQ IC50 combination: | 14.52 $\mu$M. |

Briefly, $3\times10^6$ cells/ml are stimulated with PHA+ media for 48 hours at 37° C. with 5% $CO_2$. Also, the same number of cells are incubated in PHA free media for 48 hours to serve as the negative control. At this point the cells are inoculated with the HIV-1 virus as per standard protocol. Note that in this experiment, the HIV containing supernatant from the PHA-stimulated healthy human peripheral mononuclear cells (PBMC) is not removed from the PHA-stimulated CEM/0 cell culture. Hence, the HIV-1 virus is always present in the supernatant, an experimental condition that simulates the in vivo clinical condition of newly produced and uninfected T-cells, which are always under constant exposure to HIV-1 particles. These virus particles are released by already infected T-cells and/or lymph nodes of patients.

The experimental drugs are added to the cells in the appropriate concentrations at the same time as viral inoculation or 90 minutes after the viral incubation, a time sufficient for the T-cells to be infected and start producing new HIV-1 virus particles. The control cells are resuspended in drug-free media for the duration of the exposure which lasted seven days. Aliquots of media from the control flasks only are obtained on day 5 post Rx. At day seven, three 1 ml each, aliquots of media are removed from the flasks and stored under liquid nitrogen. In addition, the remaining cells are split into three and then pelleted and stored at −80° C.

Figure 10:
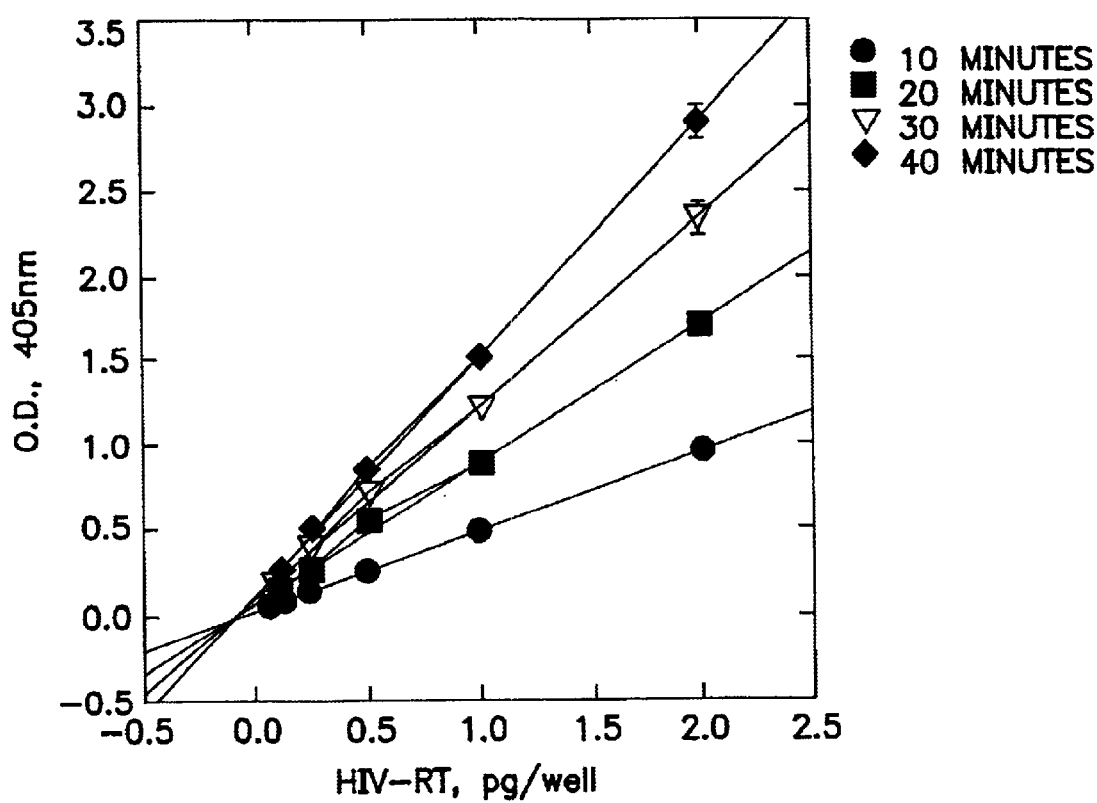
FIG. 10 represents the calibration curves for the HIV-RT Elisa assay.

The samples produced from this experiment are itemized. The cellular pellets from the 90 minute viral incubation flasks are assayed for HIV-RT using an ELISA kit for the Reverse Transcriptase Assay, non-radioactive (Boehringer Mannheim). The standard curve is determined (See FIG. 10) and the HIV-RT levels for the experimental samples are calculated. The results are shown in Table 5. It should be noted that "PEG" in Table 5 represents PEG-ASNase.

Results and Discussion: The first observation from the HIV-RT ELISA assays in these specimens from the cellular pellets of the CEM/0 T-cells is that there is diminished HIV-RT activity due to drug treatment, as compared to the untreated control cells. The most dramatic inhibition of HIV-RT is caused by AZT, a nucleoside analog reverse transcriptase inhibitor. Our initial experimental design and search for a wild-type HIV virus particle, with no mutations on HIV-RT conferring resistance to AZT, is actually shown with these results that AZT alone is very active against this viral strain.

PEG-ASNase or Saquinavir, used as a monotherapy at $IC_{50}$ concentrations, inhibited HIV-RT by 54% and 83%, respectively. These values are similar to those determined in earlier experiments.

MISID (PL-7), a new ribonucleotide reductase (RR) inhibitor, used alone at the $IC_{50}$ concentration (0.685 $\mu$M), also demonstrated a 73% inhibition of HIV-RT. This is the first evidence that a member of this class of RR inhibitors has demonstrated anti-HIV activity in addition to its anti-leukemic activity. The biochemical rationale for this class of compounds in inhibiting HIV is by depleting dNTP pools intracellularly. Lack of or reduced dNTP pools will inhibit the function of HIV-RT, in converting HIV-RNA into proviral DNA prior to integration into the mammalian genomic DNA.

Combinations of PEG+SAQ resulted in complete inhibition of HIV-RT in this experiment. Combinations of three drugs, AZT+PEG+SAQ, resulted in complete inhibition of HIV-RT in two of the three wells, and the third well's value is inhibited by 95.3% of control. The biochemical rationale of this drug combination is that AZT will inhibit further infection by HIV-RT and that this inhibition will be potentiated by the already very efficacious anti-HIV-RT effect of PEG+SAQ regimen. Since the numbers are nearing 100% inhibition of HIV-RT it is extremely difficult to demonstrate an improved inhibition by the three drug over the two drug regimen in this T-cell model system infected with a wild-type HIV virus. In experiments with HIV partially resistant to AZT, as they appear in patients, the regimen may demonstrate the validity of the above biochemical syllogism.

Combinations of four drugs, MISID+AZT+PEG+SAQ, resulted in complete inhibition of HIV-RT in two of the three wells, and the third well's value is inhibited by 95% of control. These values are superimposable to the three drug regimen, due to maximum inhibition of HIV-RT. The biochemical rational for this combination is that MISID, the RR inhibitor, will deplete dNTP pools and this will potentiate the activity of AZT-triphosphate (AZTTP), against HIV-RT. This augmented inhibitory effect will be either additive or synergistic to the already selectively synergistic effect of a protein plus protease inhibitors against this virus. Since MISID alone appears to have considerable anti-HIV-RT activity we believe that this syllogism will be shown to be correct in experiments with HIV particles resistant to one more of these classes of drugs or in patients who are infected with multi-resistant HIV variants.

Therefore, these results show that the following 3 or 4 drug regimen, of AZT+PEG+SAQ or MISID+AZT+PEG+SAQ, act synergistically against HIV-RT.

Experiment 8

Determination of the Synergistic Effect of PEG-ASNase, Saguinavir, AZT and MISID (PL-7) in CEM/0 Cell Supernatant Materials and Methods: The cell line used for this experiment is CEM/0, a human T-cell leukemic cell line. PEG-ASNase (ONCASPAR) is provided by Rhone-Poulenc Rorer. Saquinavin (SQ) is commercially available. AZT is purchased from Sigma. MISID, a ribonucleotide reductase inhibitor, is as described in Nandy P, Lien E J, Avramis V I, Med. Chem. Res. 1995, 5:664–679. RPMI-1640 media (Irvine Scientific, Irvine, Calif.), is enriched with 10% Fetal Calf Serum (Gemini Biosource, Calabasas, Calif.), 5% 1M Hepes Buffer solution and 5% Non-essential amino acids (Irvine Scientific, Irvine, Calif.). The drug concentrations used are as follows:

| | |
|---|---|
| PEG-ASNase IC50 alone: | 0.40 IU/ml |
| Saquinavir IC50 alone: | 25 $\mu$M |
| AZT | 1 $\mu$M |
| MISID | 0.685 $\mu$M |
| PEG IC50 combination: | 0.23 IU/ml |
| SAQ IC50 combination: | 14.52 $\mu$M |

Briefly, $3 \times 10^6$ cells/ml are stimulated with PHA+ media for 48 hours at 37° C. with 5% $CO_2$. Also, the same number of cells are incubated in PHA free media for 48 hours to serve as the negative control. At this point the cells are inoculated with the HIV-1 virus as per standard protocol. Note that in this experiment, the HIV containing supernatant from the PLA-stimulated healthy human peripheral mononuclear cells (PBMC) is not removed from the PHA-stimulated CEM/0 cell culture. Hence, the HIV-1 virus is always present in the supernatant, an experimental condition that simulates the in vivo clinical condition of newly produced and uninfected T-cells, which are always under constant exposure to HIV-1 particles. These virus particles are released by already infected T-cells and/or lymph nodes of patients.

The experimental drugs are added to the cells in the appropriate concentrations at the same time as viral inoculation or 90 minutes after the viral incubation, a time sufficient for the T-cells to be infected and start producing new HIV-1 virus particles. The control cells are resuspended in drug-free media for the duration of the exposure which lasted seven days. Aliquots of media from the control flasks only are obtained on day 5 post Rx. At day seven, three 1 ml each, aliquots of media are removed from the flasks and stored under liquid nitrogen. In addition, the remaining cells are split into three and then pelleted and stored at −80° C.

The samples produced from this experiment are itemized. The cell pellets of the cellular cultures (See Experiment 7) from the 90 minute viral incubation flasks are assayed for HIV-RNA quantitative assay using a kit for the assay, non-radioactive. The standard curve is determined and the HIV-RNA levels for the experimental samples are calculated as described previously.

These supernatant specimens are the ones from the cultures of the T-cell pellets of Experiment 7. These results are disclosed in Experiment 7.

The first observation from the HIV-RT ELISA assays in these specimens from the supernatants of the CEM/0 T-cells is that there is diminished HIV-RT activity on day 7 due to drug treatment, as compared to the untreated control cells on the same day. Of importance is that the untreated controls on day 5 (one value) had a higher HIV-RT O.D. than on day 7. We examined O.D. values all of which are less than the minimum quantitated concentrations based on the linearity of the calibration curve. Only one of the specimen supernatent (#7) treated with PEG-ASNase alone had an O.D. value from the assay higher than the negative control, and still lower than the average of the three untreated control culture supernatants.

Great inhibition of HIV-RT in quantitative terms (less than 66% of the Negative control value of 0.075 O.D. or 0.05 O.D.) is caused by SAQ (Specimens #9 & 10), AZT (Specimens # 11 & 13) and MISID (Specimens #15 & 16) as single agents (See Table 6. It should be noted that "PEG" in Table 6 represents PEG-ASNase.). Even greater inhibition of HIV-RT is seen by the combination of SAQ+PEG-ASNase, three specimens #17, 18 & 19, one specimen from the three drug combination of PEG-ASNase+SAQ+AZT, specimen #22, and all three specimens treated with the four drug combination regimen of PEG-ASNase+SAQ+MISID and AZT, #23, 24, & 25.

Our initial experimental design and search for a wild-type HIV virus particle, with no mutations on HIV-RT conferring resistance to AZT, is actually shown with these results that AZT alone is very active against this viral strain.

MISID, a new ribonucleotide reductase (RR) inhibitor, used alone at the $IC_{50}$ concentration (0.685 $\mu$M), also demonstrated a significant inhibition of HIV RT as a single agent and in combination with the three other drugs. This is the result in the cell pellets as well (see Experiment 7) and is the first evidence that a member of this class of RR inhibitors has demonstrated anti-HIV activity in addition to its anti-leukemic activity both intracellularly and in the supernatant specimens of these T-cell cultures.

Combinations of PEG+SAQ resulted in complete inhibition of HIV-RT in this and in the previously reported experiment in the cell pellets. In the previous experiments there is a 96% inhibition of HIV-RT (see Experiment 7). Combinations of three drugs, AZT+PEG+SAQ, resulted in complete inhibition of HIV-RT in two of the three wells, and the third well's value is inhibited by 95.3% of control, whereas in the supernatants an identical pattern is seen Specimens #20–22.

Combinations of four drugs, MISID+AZT+PEG+SAQ, resulted in complete inhibition of HIV-RT in all three of the supernatant specimens, which values correspond with the values determined in the cell pellets from the same experiment. These values are superimposable to the three drug regimen, due to maximum inhibition of HIV-RT, as we determined earlier.

The biochemical rationale for this combination is that MISID, the RR inhibitor, will deplete dNTP pools and this will potentiate the activity of AZT-triphosphate (AZTTP), against HIV-RT. This augmented inhibitory effect will be either additive or synergistic to the already selectively synergistic effect of a protein plus protease inhibitors against this virus. Since MISID alone appears to have considerable anti-HIV-RT activity we believe that this syllogism will be shown to be correct in experiments with HIV particles resistant to one or more of these classes of drugs or in patients who are infected with multi-resistant HIV variants.

Experiment 9

Determination of the Synergistic Effect of PEG-ASNase, Saguinavir, AZT and MISID (PL-7) in CEM/0 Cell Pellets The cell line used for these studies is CEM/0, a human T-cell leukemic cell line. PEG-ASNase (ONCASPAR) is provided by Rhone-Poulenc Rorer. Saquinavin is commercially available. AZT is purchased from Sigma. MISID, a ribonucleotide reductase inhibitor, is synthesized as indicated in Nandy P, Lien E J, Avramis V I, Med. Chem. Res. 1995, 5:664–679. RPMI-1640 media (Irvine Scientific, Irvine, Calif.), is enriched with 10% Fetal Calf Serum (Gemini Biosource, Calabasas, Calif.), 5% 1M Hepes Buffer solution and 5% Non-essential amino acids (Irvine Scientific, Irvine, Calif.). The drug concentrations used are as follows:

| | |
|---|---|
| PEG-ASNase IC50 alone: | 0.40 IU/ml |
| Saquinavir IC50 alone: | 25 $\mu$M |
| AZT | 1 $\mu$M |
| MISID | 0.685 $\mu$M |
| PEG IC50 combination: | 0.23 IU/ml |
| SAQ IC50 combination: | 14.52 $\mu$M. |

Briefly, $3 \times 10^6$ cells/ml are stimulated with PHA+ media for 48 hours at 37° C. with 5% $CO_2$. Also, the same number of cells are incubated in PHA free media for 48 hours to serve as the negative control. At this point the cells are inoculated with the HIV-1 virus as per standard protocol. Note that in this experiment, the HIV containing supernatant from the PHA-stimulated healthy human peripheral mononuclear cells (PBMC) is not removed from the PHA-stimulated CEM/0 cell culture. Hence, the HIV-1 virus is always present in the supernatant, an experimental condition that simulates the in vivo clinical condition of newly produced and uninfected T-cells, which are always under constant exposure to HIV-1 particles. These virus particles are released by already infected T-cells and/or lymph nodes of patients.

The experimental drugs are added to the cells in the appropriate concentrations at the same time as viral inoculation or 90 minutes after the viral incubation, a time sufficient for the T-cells to be infected and start producing new HIV-1 virus particles. The control cells are resuspended in drug-free media for the duration of the exposure which lasted seven days. Aliquots of media from the control flasks only are obtained on day 5 post Rx. At day seven, three 1 ml each, aliquots of media are removed from the flasks and stored under liquid nitrogen. In addition, the remaining cells are split into three and then pelleted and stored at –80° C.

The samples produced from this experiment are itemized. The cell pellets of the cellular cultures (see Experiment 7) from the 90 minute viral incubation flasks are assayed for HIV-RNA quantitative assay using a kit for the assay, non-radioactive. The standard curve is determined and the HIV-RNA levels for the experimental samples are calculated and reported previously.

The specimens are from the cultures of the T-cell pellets and are from the same experiment as those we reported for the HIV-RT results. These results are discussed in Experiment 7 (cell pellets) & Experiment 8 (supernatant).

Figure 11:
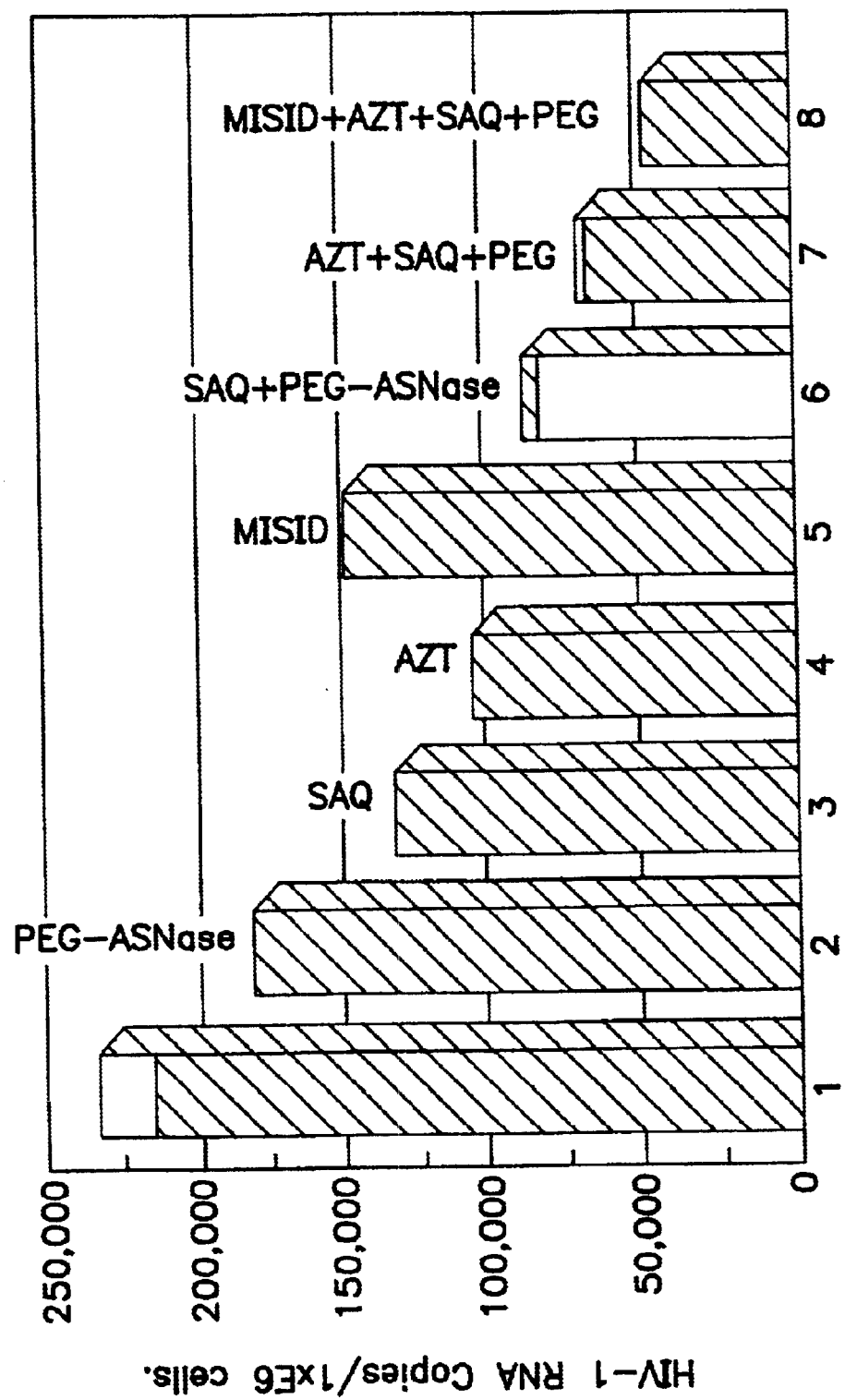
FIG. 11 represents the HIV-1 quantitative RNA assay of CEM-T-cells treated with single regimens of PEG-ASNase, Saquinavir, AZT and MISID, and combination regimens of Saquinavir and PEG-ASNase, AZT, Saquinavir and PEG-ASNase, and MISID, AZT, Saquinavir and PEG-ASNase.

The first observation from the HIV RNA quantitative assays in these specimens of CEM/0 T-cells is that there is diminished HIV RNA activity on day 7 due to drug treatment, as compared to the untreated control cells on the same day. The quantitative results are shown in Table 7 and FIG. 11. It should be noted that "PEG" in Table 7 represents PEG-ASNase.

Inhibition of HIV RNA is quantitative terms cause by AZT alone (Specimens #11–13) are greater (sensitive HIV-1 virus to AZT), with SAQ and MISID as single agents following. Greater inhibition of HIV RNA is seen by the combination of SAQ+PEG-ASNase, 38% of control, and from the three drug combination of PEG-ASNase+SAQ+AZT, 30% of control. All three specimens treated with the four drug combination regimen of PEG-ASNase+SAQ+MISID and AZT, #23, 24 & 25, has the greatest inhibition of HIV-RNA from this experiment, 20% of control, clearly showing the significant contribution of the ribonucleotide reductase inhibitor, MISID.

MISID, a new ribonucleotide reductase (RR) inhibitor, used alone at the $IC_{50}$ concentration (0.685 $\mu$M), also demonstrated a significant inhibition of HIV RNA as a single agent and most importantly, in combination with the three other drugs. This is the result in the cell pellets as well (Experiment 6) and is the repeat evidence that a member of this class of RR inhibitors has demonstrated anti-HIV activity in addition to its anti-leukemic activity both intracellularly and in the supernatant specimens of these T-cell cultures.

The biochemical rationale for this combination is that MISID, the RR inhibitor, will deplete dNTP pools and this will potentiate the activity of AZT-triphosphate (AZTTP), against HIV integration and replication, thus reduced HIV RNA. This augmented inhibitory effect will be either additive or synergistic to the already selectively synergistic effect of a protein plus protease inhibitors against this virus. Since MISID alone appears to have considerable anti-HIV RNA inhibitory activity, we believe that this syllogism will be shown to be correct in experiments with HIV particles resistant to one or more of these classes of drugs or in patients who are infected with multi-resistant HIV variants.

Experiment 10

Determination of the Synergistic Effect of PEG-ASNase, Saguinavir, AZT and MISID (PL-7) in the Suppression of HIV-RT Materials and Methods: The cell line used for these studies is CEM/0, a human T-cell leukemic cell line. PEG-ASNase (ONCASPAR) is provided by Rhone-Poulenc Rorer. Saquinavin is commercially available. AZT is purchased from Sigma. MISID, a ribonucleotide reductase inhibitor, is as described in Nandy P, Lien E J, Avramis V I, Med. Chem. Res. 1995, 5:664–679. RPMI-1640 media (Irvine Scientific, Irvine, Calif.), is enriched with 10% Fetal Calf Serum (Gemini Biosource, Calabasas, Calif.), 5% 1M Hepes Buffer solution and 5% Non-essential amino acids (Irvine Scientific, Irvine, Calif.). The drug concentrations used are as follows:

| | |
|---|---|
| PEG-ASNase IC50 alone: | 0.40 IU/ml |
| Saquinavir IC50 alone: | 25 $\mu$M |
| AZT | 1 $\mu$M |
| MISID | 0.685 $\mu$M |
| PEG IC50 combination: | 0.23 IU/ml |
| SAQ IC50 combination: | 14.52 $\mu$M |

Briefly, $3 \times 10^6$ cells/ml are stimulated with PHA+ media for 48 hours at 37° C. with 5% $CO_2$. Also, the same number of cells are incubated in PHA free media for 48 hours to serve as the negative control. At this point the cells are inoculated with the HIV-1 virus as per standard protocol. Note that in this experiment, the HIV containing supernatant from the PHA-stimulated healthy human peripheral mononuclear cells (PBMC) is not removed from the PHA-stimulated CEM/0 cell culture. Hence, the HIV-1 virus is always present in the supernatant, an experimental condition that simulates the in vivo clinical condition of newly produced and uninfected T-cells, which are always under constant exposure to HIV-1 particles. In this experiment we have seen much higher HIV-1 titers as per our control HIV-RNA in the T-cells (see Experiment 9). These virus particles are continuously released by already infected T-cells and/or lymph nodes of patients.

The experimental drugs are added to the cells in the appropriate concentrations at the same time as viral inoculation or 90 minutes after the viral incubation, a time sufficient for the T-cells to be infected and start producing new HIV-1 virus particles. The control cells are resuspended in drug-free media for the duration of the exposure which lasted seven days. Aliquots of media from the control flasks only are obtained on day 5 post Rx. At day seven, three 1 ml each, aliquots of media are removed from the flasks and stored under liquid nitrogen. In addition, the remaining cells are split into three and then pelleted and stored at –80° C. Supernatant specimens are obtained form these T-cell cultures and are frozen at –80° C. The samples produced from this experiment are itemized. The cell pellets of the cellular cultures (see Experiment 9) from the 90 minute viral incubation flasks are assayed for HIV-RNA quantitative assay using a kit for the assay, non-radioactive. We disclose here the quantitative HIV-RNA results from the supernatants of these T-cells. The standard curve is determined and the HIV-RNA levels for the experimental samples are calculated and reported previously.

Results and Discussion

These specimens are from the cultures of the T-cell pellets from the same experiment as those from which we reported the HIV-RT results (see Experiment 8) and the quantitative HIV-RNA in T-cells (see Experiment 9).

The first observation from the HIV-RNA quantitative assays in the supernatant specimens of CEM/0 T-cells is there is diminished HIV-RNA activity on day 7 due to drug treatment, as compared to the untreated control cells on the same day. The quantitative results are shown in the attached table. (Table 8). It should be noted that "PEG" in Table 8 represents PEG-ASNase. The quantitative control HIV-RNA levels (virus genomic copies/ml) are higher that from previous experiments and similar to the untreated control levels (214,445 in T-cell pellets vs. 195,483 in the supernatants).

Inhibition of HIV-RNA in quantitative terms caused by SAQ, AZT or MISID alone (Specimens #8–16), are non-statistically significant among themselves (sensitive HIV-1 virus to AZT). Similar inhibition percentages of HIV-RNA in the supernatants is seen by either the combination of SAQ+PEG-ASNase, or the three drug combination of PEG-ASNase+SAQ+AZT, in comparison to untreated control. However, all three specimens treated with the four drug combination regimen of MISID+AZT+PEG-ASNase+SAQ #23, 24 & 25, has the greatest inhibition of HIV-RNA from this experiment, 50% of control, clearly showing the significant contribution of the ribonucleotide reductase inhibitor, MISID. This latter set of data confirms the earlier observation of HIV-RNA inhibition that is shown in the T-cell pellets of 20% of control (Experiment 9). Data from the previous experimentals and this evidence indicate that the higher the HIV titer left in the supernatant, the lesser the inhibition of the virus both in the T-cells and in the supernatant would be. In other words, the data suggest that: a) these combination regimens must be given continuously under these conditions, i.e., in patients with high HIV-RNA copy number and/or viremia and b) the potentiation of the AZT+SAQ is required by either a third RT inhibitor, such as 3TC or and an RR inhibitor, such as, MISID or hydroxyurea, to potentiate the activity of AZT triphosphate (AZTTP) against HIV-RT.

MISID, a new ribonucleotide reductase (RR) inhibitor, used alone at the $IC_{50}$ concentration (0.685 $\mu$M), also demonstrated a significant inhibition of HIV-RNA as a single agent which is approximately equal to the inhibition of either SAQ or AZT. Most importantly, MISID showed it significant usefulness in combination with the three other drugs both against HIV-RT in T-cell pellets and supernatants (see Experiments 7 and 8), respectively, and in suppressing HIV-RNA left in the supernatant (Table 8). This is also the result in the T-cell pellets (see Experiments 6 and 9) and is the repeat evidence that a member of this class of RR inhibitors has demonstrated anti-HIV activity in addition to is anti-leukemic activity both introcellularly and in the supernatant specimens of these T-cell cultures.

The biochemical rationale for this combination is that MISID, the RR inhibitor, will deplete dNTP pools and this will potentiate the activity of AZTTP, against HIV-1 reverse transcription, integration and replication, thus reduced HIV-RNA. This augmented inhibitory effect will be either additive or synergistic to the already selectively synergistic effect of a protein plus protease inhibitors against this virus. Since MISID alone appears to have considerable anti-HIV-RNA inhibitory activity we believe that this syllogism will be shown to be correct in experiments with HIV particles resistant to one or more of these classes of drugs or in patients who are infected with multi-resistant HIV variants.

Experiment 10

Determination of the Synergistic Effect of PEG-ASNase, Saguinavir, AZT and 3TC on HIV-RT in CEM/0 Cell Pellets This experiment is carried out using a similar procedure, and the same concentrations of materials as in Experiment 9, however 3TC is used instead of MISID. In this experiment the exposure of HIV-RT in T-cell pellets to a combination of PEG-ASNase, Saguinavir, AZT and 3TC is measured. The results of this experiment are shown in Table 9. It should be noted that "PEG" in Table 9 represents PEG-ASNase. It is shown in Table 9 that there is some inhibition of HIV-RT by Saquinavir and PEG-ASNase alone. However, the combination of PEG-ASNase, Saquinavir, AZT and 3TC results in the complete inhibition of HIV-RT.

Experiment 11

Determination of the Synergistic Effect of PEG-ASNase, Saguinavir, AZT and 3TC on HIV-RNA in CEM/0 Cell Supernatants This experiment is carried out using a similar procedure, and the same concentrations of materials as in Experiment 10, however the exposure of HIV-RNA in T-cell supernatants to a combination of PEG-ASNase, Saquinavir, AZT and 3TC is measured. The results of this experiment are shown in Table 10. It should be noted that "PEG" in Table 10 represents PEG-ASNase. It is shown in Table 10 that there is some inhibition of HIV-RNA by Saquinavir and PEG-ASNase alone (approximately 55% and 73% of control, respectively). The combination of PEG-ASNase, Saquinavir, and AZT results in the greater inhibition of HIV-RNA (approximately 21% of control). However, the combination of PEG-ASNase, Saquinavir, AZT and 3TC results in the complete inhibition of HIV-RNA (0% of control)(see Table 10).

The present invention may be embodied in other specific forms without departing from the spirit or essential attributes thereof.

TABLE 1

| # | Accession # | Patient ID | Notes | Results N* | Log 10 N |
|---|---|---|---|---|---|
| 1 | 00186 | Pellet 1/7/98 | flask #1, ccm/0, +PHA | 43,615 | 4.64 |
| 2 | 00187 | Pellet 1/7/98 | flask #2, ccm/0, +PHA | Unable to Quantitate | — |
| 3 | 00188 | Pellet 1/7/98 | flask #3, ccm/0, +PHA | 186,295 | 5.27 |
| 4 | 00189 | Pellet 1/7/98 | flask #4, ccm/0, +PHA | Unable to Quantitate | — |
| 5 | 00190 | Pellet 1/7/98 | | 123,544 | 5.09 |
| 6 | 00191 | Pellet 1/7/98 | | Unable to Quantitate | — |
| 7 | 00192 | Pellet 1/7/98 | | 114,048 | 5.06 |
| 8 | 00193 | Pellet 1/7/98 | | Unable to Quantitate | |
| 9 | 00194 | Pellet 1/7/98 | | 182,841 | 5.26 |
| 10 | 00195 | Pellet 1/7/98 | | Unable to Quantitate | — |
| 11 | 00196 | Pellet 1/7/98 | | 264,801 | 5.42 |
| 12 | 00197 | Pellet 1/7/98 | | Unable to Quantitate | — |
| 13 | 00198 | Pellet 1/7/98 | | Unable to Quantitate | — |
| 14 | | | | | |
| 15 | | | | | |
| 16 | | | | | |
| 17 | | | | | |
| 18 | | | | | |

*N is the number of virus genomic copies/mL of supernatant or copies/cell pellet. Dynamic range of the HIV-1 Monitor Assay is 400 to 750,000 copies/ml. Inquire with laboratory if quantitation below 400 copies/mL is needed.

TABLE 2

SPECIMEN INVENTORY FOR HIV RNA ASSAYS
TOTAL 13 CELLULAR PELLETS FOR HIV-RNA ASSAY

| Code # | Specimen Type | Conditions | N copies/cell pellet | Log 10 N |
|---|---|---|---|---|
| 1 | PELLET | FLASK #1, CEM/0, +PHA | 43615 | 4.64 |
| 2 | PELLET | FLASK #2, CEM/0, +PHA | | |
| 3 | PELLET | FLASK #3, CEM/0, +PHA | 186295 | 5.27 |
| 4 | PELLET | FLASK #4, CEM/0, +PHA | | |
| 5 | PELLET | FLASK #8, CEM/0, +PHA, +PEG | | |
| 6 | PELLET | FLASK #9, CEM/0, +PHA, +PEG | 182841 | 5.26 |
| 7 | PELLET | FLASK #10, CEM/0, +PHA, +PEG | 264801 | 5.42 |
| 8 | PELLET | FLASK #11, CEM/0, +PHA, +SAQ | 114048 | 5.06 |
| 9 | PELLET | FLASK #12, CEM/0, +PHA, +SAQ | | |
| 10 | PELLET | FLASK #13, CEM/0, +PHA, +SAQ | 123544 | 5.09 |
| 11 | PELLET | FLASK #14, CEM/0, +PHA, +PEG, +SAQ | | |
| 12 | PELLET | FLASK #15, CEM/0, +PHA, +PEG, +SAQ | | |
| 13 | PELLET | FLASK #16, CEM/0, +PHA, +PEG, +SAQ | | |

TABLE 2a

SAMPLE LOG FOR HIV-RT ASSAY #4
Standard Curve Y = 0.5955(X) + 0.09363 r = 0.9967

| TEST | TYPE | CONDITIONS | VOL, ml | O.D. 405 | HIV-RT pg/well | % cont. | |
|---|---|---|---|---|---|---|---|
| 1 | PELLET | FLASK #1 CEM/O, +PHA | 1.00 | 0.352 | 0.434 | | |
| 2 | PELLET | FLASK #2, CEM/O, +PHA | 1.00 | 0.431 | 0.567 | | |
| 3 | PELLET | FLASK #3, CEM/O, +PHA | 1.00 | 0.346 | 0.424 | | |
| 4 | PELLET | FLASK #4, CEM/O, +PHA | 1.00 | 0.321 | 0.382 | | |
| 5 | PELLET | FLASK #5, CEM/O, −PHA | 1.00 | 0.103 | 0.016 | 3.87 | X2 = 4.00 +/− 0.18 pg/well, % CV = 4.42% |
| 6 | PELLET | FLASK #6, CEM/O, −PHA | 1.00 | 0.104 | 0.017 | 4.12 | |
| 7 | PELLET | FLASK #7, CEM/O, −PHA | 1.00 | 0.094 | 0.001 | 0.24 | |
| 8 | PELLET | FLASK #8, CEM/O, +PHA, +PEG | 1.00 | 0.29 | 0.330 | 79.9 | X3 = 68.43 +/− 11.26 pg/well, % CV = 16.45% |

TABLE 2a-continued

SAMPLE LOG FOR HIV-RT ASSAY #4
Standard Curve Y = 0.5955(X) + 0.09363 r = 0.9967

| TEST | TYPE | CONDITIONS | VOL, ml | O.D. 405 | HIV-RT pg/well | % cont. | |
|---|---|---|---|---|---|---|---|
| 9 | PELLET | FLASK #9, CEM/O, +PHA, +PEG | 1.00 | 0.261 | 0.281 | 68.0 | |
| 10 | PELLET | FLASK #10, CEM/O, +PHA, +PEG | 1.00 | 0.235 | 0.237 | 57.4 | |
| 11 | PELLET | FLASK #11, CEM/O, +PHA, +SAQ | 1.00 | 0.178 | 0.142 | 34.4 | X2 = 31.10 +/− 4.67 pg/well, % CV = 15.01% |
| 12 | PELLET | FLASK #12, CEM/O, +PHA, +SAQ | 1.00 | 0.162 | 0.115 | 27.8 | |
| 13 | PELLET | FLASK #13, CEM/O, +PHA, +SAQ | 1.00 | 0.083 | −0.180 | 0 | |
| 14 | PELLET | FLASK #14, CEM/O, +PHA, +PEG, +SAQ | 1.00 | 0.132 | 0.064 | 15.5 | X3 = 17.77 +/− 2.08 pg/well, % CV = 11.73% |
| 15 | PELLET | FLASK #15, CEM/O, +PHA, +PEG, +SAQ | 1.00 | 0.138 | 0.075 | 18.2 | |
| 16 | PELLET | FLASK #16, CEM/O, +PHA, +PEG, +SAQ | 1.00 | 0.142 | 0.081 | 19.6 | |

TABLE 3

RESULTS FROM HIV MONITOR ASSAY
SUPERNATANTS OBTAINED
SUPERNATANTS

| Code # | Specimen Type* | Condition | N | Log 10 N | MEAN N | S.D. | % CONTROL |
|---|---|---|---|---|---|---|---|
| 1 | SUPER | FLASK #1, CEM/O, +PHA | 76884 | 4.89 | | | |
| 2 | SUPER | FLASK #2, CEM/O, +PHA | 48109 | 4.68 | | | |
| 3 | SUPER | FLASK #3, CEM/O, +PHA | 183128 | 5.26 | | | |
| 4 | SUPER | FLASK #4, CEM/O, +PHA | 49140 | 4.69 | 130006 | 75126 | 100 |
| 5 | SUPER | FLASK #8, CEM/O, +PHA, +PEG | 51765 | 4.71 | | | |
| 6 | SUPER | FLASK #9, CEM/O, +PHA, +PEG | 53029 | 4.72 | | | |
| 7 | SUPER | FLASK #10, CEM/O, +PHA, +PEG | 54267 | 4.73 | 53020 | 1251 | 40.78 |
| 8 | SUPER | FLASK #11, CEM/O, +PHA +SAQ | 40719 | 4.61 | | | |
| 9 | SUPER | FLASK #12, CEM/O, +PHA +SAQ | 39978 | 4.60 | | | |
| 10 | SUPER | FLASK #13, CEM/O, +PHA +SAQ | 45602 | 4.66 | 42100 | 3056 | 32.38 |
| 11 | SUPER | FLASK #14, CEM/O, +PHA +PEG, +SAQ | 32908 | 4.52 | | | |
| 12 | SUPER | FLASK #15, CEM/O, +PHA +PEG, +SAQ | 31441 | 4.50 | | | |
| 13 | SUPER | FLASK #16, CEM/O, +PHA +PEG, +SAQ | 30454 | 4.48 | 31601 | 1235 | 24.31 |

*HIV virus was NOT removed from the media. HIV-1 virus can not be "killed" by these drugs outside of a T-cell. Thus, the lower level of HIV in the supernatant of PEG-ASNase and SAQ is due to loss of HIV by infection and non-regeneration by the T-cells.
This observation fits well with the cell pellet data of non-detectable intracellular HIV RNA

TABLE 4

| # | Accession # | Patient ID | Notes | N* | Log 10 N |
|---|---|---|---|---|---|
| 1 | 201 | Supernatant #1 | | 45,602 | 4.66 |
| 2 | 202 | Supernatant #2 | | 53,029 | 4.72 |
| 3 | 203 | Supernatant #3 | | 40,719 | 4.61 |
| 4 | 204 | Supernatant #4 | | 49,140 | 4.69 |
| 5 | 205 | Supernatant #5 | | 54,267 | 4.73 |
| 6 | 206 | Supernatant #6 | | 39,978 | 4.60 |
| 7 | 207 | Supernatant #7 | | 51,765 | 4.71 |
| 8 | 208 | Supernatant #8 | | 76,884 | 4.89 |
| 9 | 209 | Supernatant #9 | | 30,454 | 4.48 |
| 10 | 210 | Supernatant #10 | | 183,128 | 5.26 |
| 11 | 211 | Supernatant #11 | | 48,109 | 4.68 |
| 12 | 212 | Supernatant #12 | | 31,441 | 4.50 |
| 13 | 213 | Supernatant #13 | | 32,908 | 4.52 |
| 14 | | | | | |
| 15 | | | | | |
| 16 | | | | | |
| 17 | | | | | |
| 18 | | | | | |

*N is the number of virus genomic copies/mL of supernatant or copies/cell pellet. Dynamic range of the HIV-1 Monitor Assay is 400 to 750,000 copies/ml. Inquire with laboratory if quantitation below 400 copies/mL is needed.

TABLE 5

SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION 90 MIN INCUBATION AND DRUG EXPOSURE
CELL PELLET DAY 7 POST Rx
ELISA ASSAY
STANDARD CURVE Y = 1.13X + 0.100 r = 0.999

| CODE | TYPE | CONDITIONS | O.D. | HIV-RT pg/well | pg/well | MEAN | S.D. | % of control | RANGE | S.D. | % of control |
|---|---|---|---|---|---|---|---|---|---|---|---|
| HH1 | PELLET | PHA + NO Rx DRUG-FREE MEDIA, CONTROL | 0.219 | 0.107 | 0.107 | | | | | | |
| HH2 | PELLET | PHA + NO Rx DRUG-FREE MEDIA, CONTROL | 0.267 | 0.150 | 0.150 | | | | | | |
| HH3 | PELLET | PHA + NO Rx DRUG-FREE MEDIA, CONTROL | 0.216 | 0.104 | 0.104 | | | | | | |
| HH4 | PELLET | PHA + NO Rx DRUG-FREE MEDIA, CONTROL | 0.510 | 0.368 | 0.368 | 0.182 | 0.13 | 100 | — | — | — |
| AA1 | PELLET | PEG 0.400 IU/ml | 0.196 | 0.085 | 0.086 | | | | | | |
| AA2 | PELLET | PEG 0.400 IU/ml | 0.194 | 0.084 | 0.084 | | | | | | |
| AA3 | PELLET | PEG 0.400 IU/ml | 0.106 | 0.005 | 0.005 | 0.058 | 0.05 | 46.03 | 0.085 | 0.001 | 67.46 |
| BB1 | PELLET | SAQ 25 uM | 0.109 | 0.008 | 0.008 | | | | | | |
| BB2 | PELLET | SAQ 25 uM | 0.111 | 0.010 | 0.010 | | | | | | |
| BB3 | PELLET | SAQ 25 uM | 0.132 | 0.029 | 0.029 | 0.016 | 0.01 | 12.7 | — | — | 12.7 |
| CC1 | PELLET | AZT 1 uM | 0.086 | −0.013 | 0 | | | | | | |
| CC2 | PELLET | AZT 1 uM | 0.092 | −0.007 | 0 | | | | | | |
| CC3 | PELLET | AZT 1 uM | 0.076 | −0.022 | 0 | 0 | — | 0 | — | — | 0 |
| DD1 | PELLET | PL-7 0.685 uM | 0.174 | 0.066 | 0.066 | | | | | | |
| DD2 | PELLET | PL-7 0.685 uM | 0.141 | 0.037 | 0.037 | | | | | | |
| DD3 | PELLET | PL-7 0.685 uM | 0.080 | −0.018 | 0 | 0.34 | 0.03 | 26.98 | 0.052 | 0.021 | 41.27 |
| EE1 | PELLET | PEG 0.233 IU/ml + SAQ 14.52 uM | 0.067 | −0.030 | 0 | | | | | | |
| EE2 | PELLET | PEG 0.233 IU/ml + SAQ 14.52 uM | 0.094 | −0.005 | 0 | | | | | | |
| EE3 | PELLET | PEG 0.233 IU/ml + SAQ 14.52 uM | 0.050 | −0.054 | 0 | 0 | — | 0 | — | — | 0 |
| FF1 | PELLET | PEG 0.233 IU/ml + SAQ 14.52 uM + AZT 1 uM | 0.040 | −0.045 | 0 | | | | | | |
| FF2 | PELLET | PEG 0.233 IU/ml + SAQ 14.52 uM + AZT 1 uM | 0.027 | −0.066 | 0 | | | | | | |
| FF3 | PELLET | PEG 0.233 IU/ml + SAQ 14.52 uM + AZT 1 uM | 0.119 | 0.017 | 0.017 | 0.006 | 0.010 | 4.76* | 0.017 | — | 13.49* |
| GG1 | PELLET | PEG 0.233 IU/ml + SAQ 14.52 uM + AZT 1 uM + PL-7 0.685 uM | 0.124 | 0.022 | 0.022 | | | | | | |
| GG2 | PELLET | PEG 0.233 IU/ml + SAQ 14.52 uM + AZT 1 uM + PL-7 0.685 uM | 0.086 | −0.013 | 0 | | | | | | |
| GG3 | PELLET | PEG 0.233 IU/ml + SAQ 14.52 uM + AZT 1 uM + PL-7 0.685 uM | 0.099 | −0.001 | 0 | 0.007 | 0.001 | 5.56* | 0.022 | — | 17.46* |
| | | NEGATIVE CONTROL | 0.078 | −0.020 | — | — | — | — | — | — | — |

*SIGNIFIES A SINGLE POINT DETERMINATION WHERE THE OTHER TWO POINTS WERE ZERO.

TABLE 6

SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION, CONCURRENT DRUG EXPOSURE
SUPERNATANTS FROM THE CELL SUSPENSION, DAY 7 POST Rx,
ELISA ASSAY
STANDARD CURVE Y = 0.73795 (X) + 0.3006 r = 0.99962

| TEST # | CODE | TYPE | CONDITIONS | O.D. | HIV-RT pg/well | HIV-RT pg/well |
|---|---|---|---|---|---|---|
| 1 | HH1 | SUPER | PHA + NO Rx DRUG-FREE MEDIA, CONTROL | 0.136 | −0.223 | 0 |
| 2 | HH2 | SUPER | PHA + NO Rx DRUG-FREE MEDIA, CONTROL | 0.124 | −0.239 | 0 |
| 3 | HH3 | SUPER | PHA + NO Rx DRUG-FREE MEDIA, CONTROL | 0.109 | −0.259 | 0 |
| 4 | HH4 | SUPER | PHA + NO Rx DRUG-FREE MEDIA, CONTROL | 0.059 | −0.327 | 0 |
| 5 | AA1 | SUPER | PEG 0.400 IU/Ml | 0.058 | −0.328 | 0 |
| 6 | AA2 | SUPER | PEG 0.400 IU/Ml | 0.071 | −0.310 | 0 |
| 7 | AA3 | SUPER | PEG 0.400 IU/Ml | 0.091 | −0.283 | 0 |
| 8 | BB1 | SUPER | SAQ 25 uM | 0.054 | −0.333 | 0 |
| 9 | BB2 | SUPER | SAQ 25 uM | 0.034 | −0.361 | 0 |
| 10 | BB3 | SUPER | SAQ 25 uM | 0.043 | −0.348 | 0 |
| 11 | CC1 | SUPER | AZT 1 uM | 0.044 | −0.347 | 0 |
| 12 | CC2 | SUPER | AZT 1 uM | 0.066 | −0.317 | 0 |
| 13 | CC3 | SUPER | AZT 1 uM | 0.049 | −0.340 | 0 |
| 14 | DD1 | SUPER | MISID 0.685 uM | 0.051 | −0.338 | 0 |

TABLE 6-continued

SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION, CONCURRENT DRUG EXPOSURE
SUPERNATANTS FROM THE CELL SUSPENSION, DAY 7 POST Rx,
ELISA ASSAY
STANDARD CURVE Y = 0.73795 (X) + 0.3006 r = 0.99962

| TEST # | CODE | TYPE | CONDITIONS | O.D. | HIV-RT pg/well | HIV-RT pg/well |
|---|---|---|---|---|---|---|
| 15 | DD2 | SUPER | MISID 0.685 uM | 0.039 | −0.354 | 0 |
| 16 | DD3 | SUPER | MISID 0.685 uM | 0.038 | −0.355 | 0 |
| 17 | EE1 | SUPER | PEG 0.233 IU/ml + SAQ 14.52 uM | 0.047 | −0.343 | 0 |
| 18 | EE2 | SUPER | PEG 0.233 IU/ml + SAQ 14.52 uM | 0.039 | −0.354 | 0 |
| 19 | EE3 | SUPER | PEG 0.233 IU/ml + SAQ 14.52 uM | 0.019 | −0.381 | 0 |
| 20 | FF1 | SUPER | PEG 0.233 IU/ml + SAQ 14.52 uM + AZT 1 uM | 0.063 | −0.321 | 0 |
| 21 | FF2 | SUPER | PEG 0.233 IU/ml + SAQ 14.52 uM + AZT 1 uM | 0.043 | −0.347 | 0 |
| 22 | FF3 | SUPER | PEG 0.233 IU/ml + SAQ 14.52 uM + AZT 1 uM | 0.023 | −0.375 | 0 |
| 23 | GG1 | SUPER | PEG 0.233 IU/ml + SAQ 14.52 uM + MISID 0.685 uM + 1 uM AZT | 0.024 | −0.374 | 0 |
| 24 | GG2 | SUPER | PEG 0.233 IU/ml + SAQ 14.52 uM + MISID 0.685 uM + 1 uM AZT | 0.036 | −0.358 | 0 |
| 25 | GG3 | SUPER | PEG 0.233 IU/ml + SAQ 14.52 uM + MISID 0.685 uM + 1 uM AZT | 0.048 | −0.342 | 0 |
| 26 | HH1 | SUPER | CONTROL, DAY 5 POST VIRAL INFECTION | 0.293 | −0.010 | 0 |
|  |  |  | Negative CONTROL | 0.075 | −0.305 | 0 |

TABLE 7

SPECIMEN LOG FOR ANTI-HIV DRUG SYNERGY STUDIES.
SAMPLES TO BE RUN FOR HIV-RNA

| | CODE | TYPE | CONDITIONS | N* | mean, X3 | S.D. | % control |
|---|---|---|---|---|---|---|---|
| 1 | | PELLET | PHA + NO Rx DRUG-FREE MEDIA, CONTROL | 202837 | | | |
| 2 | | PELLET | PHA + NO Rx DRUG-FREE MEDIA, CONTROL | 189247 | | | |
| 3 | | PELLET | PHA + NO Rx DRUG-FREE MEDIA, CONTROL | 270339 | | | |
| 4 | | PELLET | PHA + NO Rx DRUG-FREE MEDIA, CONTROL | 195395 | 214455 | 37668 | 100 |
| 5 | | PELLET | PEG 0.400 IU/ml | 183977 | | | |
| 6 | | PELLET | PEG 0.400 IU/ml | 156304 | | | |
| 7 | | PELLET | PEG 0.400 IU/ml | 180062 | 173448 | 14975 | 81 |
| 8 | | PELLET | SAQ 25 uM | 138583 | | | |
| 9 | | PELLET | SAQ 25 uM | 109522 | | | |
| 10 | | PELLET | SAQ 25 uM | 128780 | 125628 | 14785 | 59 |
| 11 | | PELLET | AZT 1 uM | 107269 | | | |
| 12 | | PELLET | AZT 1 uM | 97933 | | | |
| 13 | | PELLET | AZT 1 uM | 102217 | 102473 | 4673 | 48 |
| 14 | | PELLET | MISID 0.685 uM | 149650 | | | |
| 15 | | PELLET | MISID 0.685 uM | 146865 | | | |
| 16 | | PELLET | MISID 0.685 uM | 143816 | 146777 | 2918 | 68 |
| 17 | | PELLET | PEG 0.233 IU/ml + SAQ 14.52 uM | 94130 | | | |
| 18 | | PELLET | PEG 0.233 IU/ml + SAQ 14.52 uM | 78783 | | | |
| 19 | | PELLET | PEG 0.233 IU/ml + SAQ 14.52 uM | 73219 | 82044 | 10830 | 38 |
| 20 | | PELLET | PEG 0.233 IU/ml + SAQ 14.52 uM + AZT 1 uM | 68598 | | | |
| 21 | | PELLET | PEG 0.233 IU/ml + SAQ 14.52 uM + AZT 1 uM | 68597 | | | |
| 22 | | PELLET | PEG 0.233 IU/ml + SAQ 14.52 uM + AZT 1 uM | 58143 | 65113 | 6036 | 30 |
| 23 | | PELLET | PEG 0.233 IU/ml + SAQ 14.52 uM + MISID 0.685 uM + AZT 1 uM | 36057 | | | |
| 24 | | PELLET | PEG 0.233 IU/ml + SAQ 14.52 uM + MISID 0.685 uM + AZT 1 uM | 43115 | | | |
| 25 | | PELLET | PEG 0.233 IU/ml + SAQ 14.52 uM + MISID 0.685 uM + AZT 1 uM | 48338 | 42503 | 6163 | 20 |

TABLE 8

SPECIMEN LOG FOR ANTI-HIV DRUG SYNERGY STUDIES.
SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION FOR 90 MINS., DRUG EXPOSURE
SUPERNATANTS FROM THE CELL SUSPENSION, DAY 7 POST Rx,
ELISA ASSAY

| TEST # | CODE | TYPE | CONDITIONS | N* | MEAN | % OF CONTROL |
|---|---|---|---|---|---|---|
| 1 | HH1 | SUPER | PHA + NO Rx DRUG-FREE MEDIA, CONTROL | 209819 | | |
| 2 | HH2 | SUPER | PHA + NO Rx DRUG-FREE MEDIA, CONTROL | 211254 | | |
| 3 | HH3 | SUPER | PHA + NO Rx DRUG-FREE MEDIA, CONTROL | 187126 | | |
| 4 | HH4 | SUPER | PHA + NO Rx DRUG-FREE MEDIA, CONTROL | 173734 | 195483 | 100.00 |

TABLE 8-continued

SPECIMEN LOG FOR ANTI-HIV DRUG SYNERGY STUDIES.
SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION FOR 90 MINS., DRUG EXPOSURE
SUPERNATANTS FROM THE CELL SUSPENSION, DAY 7 POST Rx,
ELISA ASSAY

| TEST # | CODE | TYPE | CONDITIONS | N* | MEAN | % OF CONTROL |
|---|---|---|---|---|---|---|
| 5 | AA1 | SUPER | PEG 0.400 IU/ml | 147041 | | |
| 6 | AA2 | SUPER | PEG 0.400 IU/ml | 142575 | | |
| 7 | AA3 | SUPER | PEG 0.400 IU/ml | 141667 | 143761 | 73.54 |
| 8 | BB1 | SUPER | SAQ 25 uM | 122515 | | |
| 9 | BB2 | SUPER | SAQ 25 uM | 128455 | | |
| 10 | BB3 | SUPER | SAQ 25 uM | 123316 | 124762 | 63.82 |
| 11 | CC1 | SUPER | AZT 1 uM | 120981 | | |
| 12 | CC2 | SUPER | AZT 1 uM | 121288 | | |
| 13 | CC3 | SUPER | AZT 1 uM | 119805 | 120691 | 61.74 |
| 14 | DD1 | SUPER | MISID 0.685 uM | 133837 | | |
| 15 | DD2 | SUPER | MISID 0.685 uM | 133772 | | |
| 16 | DD3 | SUPER | MISID 0.685 uM | 133231 | 133613 | 68.35 |
| 17 | EE1 | SUPER | PEG 0.233 IU/ml + SAQ 14.52 uM | 119606 | | |
| 18 | EE2 | SUPER | PEG 0.233 IU/ml + SAQ 14.52 uM | 119565 | | |
| 19 | EE3 | SUPER | PEG 0.233 IU/ml + SAQ 14.52 uM | 119595 | 119589 | 61.18 |
| 20 | FF1 | SUPER | PEG 0.233 IU/ml + SAQ 14.52 uM + AZT 1 uM | 114487 | | |
| 21 | FF2 | SUPER | PEG 0.233 IU/ml + SAQ 14.52 uM + AZT 1 uM | 118734 | | |
| 22 | FF3 | SUPER | PEG 0.233 IU/ml + SAQ 14.52 uM + AZT 1 uM | 113882 | 115701 | 59.19 |
| 23 | GG1 | SUPER | PEG 0.233 IU/ml + SAQ 14.52 uM + MISID 0.685 uM + 1 uM AZT | 111511 | | |
| 24 | GG2 | SUPER | PEG 0.233 IU/ml + SAQ 14.52 uM + MISID 0.685 uM + 1 uM AZT | 91918 | | |
| 25 | GG3 | SUPER | PEG 0.233 IU/ml + SAQ 14.52 uM + MISID 0.685 uM + 1 uM AZT | 85373 | 96267 | 49.25 |
| 26 | D5 | SUPER | CONTROL, DAY 5 POST VIRAL INFECTION | 137413 | | |

TABLE 9

SPECIMEN LOG FOR HIV-RT ELISA ASSAY
EXPERIMENTAL DESIGN:
CEM/O CELLS, PHA STIMULATION, 48 HOURS
CEM/O CELLS, VIRAL INNOCULATION, +/- 90 MINS., DRUG EXPOSURE
PELLETS AND SUPERNATANTS FROM THE CELL SUSPENSION, DAY 7 POST Rx,
ELISA ASSAY
STANDARD CURVE Y = 0.75847(X) + 0.07792 r = 0.99914

| CODE | TYPE | CONDITIONS | O.D. | HIV-RT ng/well | HIV-RT ng/well | MEAN X3 |
|---|---|---|---|---|---|---|
| PBMC | PELLET | PBMC CELLS INFECTED FOR TRANSFECTION | 0.669 | 0.779 | 0.779 | 0.779 |
| HH1 | PELLET | NO Rx DRUG-FREE MEDIA, CONTROL | 0.424 | 0.456 | 0.456 | |
| HH2 | PELLET | NO Rx DRUG-FREE MEDIA, CONTROL | 0.332 | 0.335 | 0.335 | |
| HH3 | PELLET | NO Rx DRUG-FREE MEDIA, CONTROL | 0.317 | 0.315 | 0.315 | 0.369 |
| AA1 | PELLET | PEG 0.400 IU/ml | 0.23 | 0.201 | 0.201 | |
| AA2 | PELLET | PEG 0.400 IU/ml | 0.186 | 0.142 | 0.142 | |
| AA3 | PELLET | PEG 0.400 IU/ml | 0.179 | 0.133 | 0.133 | 0.159 |
| BB1 | PELLET | SAQ 25 uM | 0.094 | 0.021 | 0.021 | |
| BB2 | PELLET | SAQ 25 uM | 0.095 | 0.023 | 0.023 | |
| BB3 | PELLET | SAQ 25 uM | 0.095 | 0.023 | 0.023 | 0.022 |
| CC1 | PELLET | AZT 1 uM | 0.04 | −0.050 | 0 | |
| CC2 | PELLET | AZT 1 uM | 0.042 | −0.047 | 0 | |
| CC3 | PELLET | AZT 1 uM | 0.058 | −0.026 | 0 | 0 |
| DD1 | PELLET | 3TC 1 uM | 0.077 | −0.001 | 0 | |
| DD2 | PELLET | 3TC 1 uM | 0.077 | −0.001 | 0 | |
| DD3 | PELLET | 3TC 1 uM | 0.087 | 0.012 | 0.012 | 0.004 |
| EE1 | PELLET | PEG 0.233 IU/ML + SAQ 14.52 uM | 0.045 | −0.043 | 0 | |
| EE2 | PELLET | PEG 0.233 IU/ML + SAQ 14.52 uM | 0.042 | −0.047 | 0 | |
| EE3 | PELLET | PEG 0.233 IU/ML + SAQ 14.52 uM | 0.035 | −0.057 | 0 | 0 |
| FF1 | PELLET | PEG 0.233 IU/ML + SAQ 14.52 uM + AZT 1 uM | 0.024 | −0.071 | 0 | |
| FF2 | PELLET | PEG 0.233 IU/ML + SAQ 14.52 uM + AZT 1 uM | 0.021 | −0.075 | 0 | |
| FF3 | PELLET | PEG 0.233 IU/ML + SAQ 14.52 uM + AZT 1 uM | 0.028 | −0.066 | 0 | 0 |
| GG1 | PELLET | PEG 0.233 IU/ML + SAQ 14.52 uM + AZT 1 uM + 3TC 1 uM | 0.017 | −0.080 | 0 | |
| GG2 | PELLET | PEG 0.233 IU/ML + SAQ 14.52 uM + AZT 1 uM + 3TC 1 uM | 0.018 | −0.079 | 0 | |
| GG3 | PELLET | PEG 0.233 IU/ML + SAQ 14.52 uM + AZT 1 uM + 3TC 1 uM | 0.005 | −0.096 | 0 | 0 |

TABLE 10

SPECIMEN LOG FOR ANTI-HIV DRUG SYNERGY STUDIES.
SPECIMEN LOG FOR ANTI-HIV DRUG SYNERGY STUDIES.
EXPERIMENTAL DESIGN:
CEM/O CELLS, PHA STIMULATION, 48 HOURS
CEM/O CELLS, VIRAL INNOCULATION FOR 90 MINS., DRUG EXPOSURE
SUPERNATANTS FROM THE CELL SUSPENSION, DAY 7 POST Rx,
ELISA ASSAY
HIV-RNA ASSAY

| TEST # | CODE | TYPE | CONDITIONS | N* | MEAN | % OF CONTROL |
|---|---|---|---|---|---|---|
| 1 | PBMC | SUPER | VIRAL SUPERNATANT | 5584 | | |
| 2 | HH1 | SUPER | PHA + NO Rx DRUG-FREE MEDIA, CONTROL | 4927 | | |
| 3 | HH2 | SUPER | PHA + NO Rx DRUG-FREE MEDIA, CONTROL | 4627 | | |
| 4 | HH3 | SUPER | PHA + NO Rx DRUG-FREE MEDIA, CONTROL | 3722 | 4425 | 100.00 |
| 5 | AA1 | SUPER | PEG 0.400 IU/ml | 3132 | | |
| 6 | AA2 | SUPER | PEG 0.400 IU/ml | 3048 | | |
| 7 | AA3 | SUPER | PEG 0.400 IU/ml | 3520 | 3233 | 73.06 |
| 8 | BB1 | SUPER | SAQ 25 uM | 2816 | | |
| 9 | BB2 | SUPER | SAQ 25 uM | 2375 | | |
| 10 | BB3 | SUPER | SAQ 25 uM | 2122 | 2438 | 55.08 |
| 11 | CC1 | SUPER | AZT 1 uM | 1203 | | |
| 12 | CC2 | SUPER | AZT 1 uM | 1409 | | |
| 13 | CC3 | SUPER | AZT 1 uM | 1700 | 1437 | 32.48 |
| 14 | DD1 | SUPER | 3TC 1 uM | 1700 | | |
| 15 | DD2 | SUPER | 3TC 1 uM | 1836 | | |
| 16 | DD3 | SUPER | 3TC 1 uM | 1719 | 1752 | 39.58 |
| 17 | EE1 | SUPER | PEG 0.233 IU/ml + SAQ 14.52 uM | 1992 | | |
| 18 | EE2 | SUPER | PEG 0.233 IU/ml + SAQ 14.52 uM | 2083 | | |
| 19 | EE3 | SUPER | PEG 0.233 IU/ml + SAQ 14.52 uM | 1991 | 2022 | 45.69 |
| 20 | FF1 | SUPER | PEG 0.233 IU/ml + SAQ 14.52 uM + AZT 1 uM | 743 | | |
| 21 | FF2 | SUPER | PEG 0.233 IU/ml + SAQ 14.52 uM + AZT 1 uM | 1118 | | |
| 22 | FF3 | SUPER | PEG 0.233 IU/ml + SAQ 14.52 uM + AZT 1 uM | 0 | 931 | 21.03 |
| 23 | GG1 | SUPER | PEG 0.233 IU/ml + SAQ 14.52 uM + AZT 1 uM + 3TC 1 uM | 0 | | |
| 24 | GG2 | SUPER | PEG 0.233 IU/ml + SAQ 14.52 uM + AZT 1 uM + 3TC 1 uM | 0 | | |
| 25 | GG3 | SUPER | PEG 0.233 IU/ml + SAQ 14.52 uM + AZT 1 uM + 3TC 1 uM | 0 | 0 | 0.00 |

What is claimed is:

1. A method of treating Human Immunodeficiency Virus (HIV) infection, comprising administering to a patient, in need thereof, a composition comprising a synergistically effective combination of:
 a PEG-ASNase compound and Saquinavir, or pharmaceutically acceptable salts thereof, in amounts that are effective to inhibit the T-Cell synthesis of enzymes required for the competent replication and assembly of the Human Immunodeficiency Virus.

2. A method according to claim 1 wherein administering said PEG-ASNase compound and said Saquinavir is concurrent.

3. A method according to claim 1 wherein administering said PEG-ASNase compound and said Saquinavir is sequential.

4. A pharmaceutical composition comprising a synergistically effective combination of a PEG-ASNase compound and Saquinavir or pharmaceutically acceptable salts thereof, and a pharmaceutically acceptable carrier.

5. A method of inhibiting or treating Human Immunodeficiency Virus (HIV) infection, comprising administering to a patient, in need thereof, an amount of a composition comprising a synergistically effective combination of:
 a PEG-ASNase compound and Saquinavir, or pharmaceutically acceptable salts thereof, in amounts that are effective to inhibit the T-Cell synthesis of enzymes required for the competent replication and assembly of the Human Immunodeficiency Virus (HIV), and optionally including a synergistically effective amount of AZT or synergistically effective amounts of AZT and MISID or 3TC, or pharmaceutically acceptable salts thereof.

6. A method of limiting the spread of HIV infection comprising the step of exposing a cell population infected with HIV to a composition comprising a synergistically effective combination of:
 a PEG-ASNase compound and Saquinavir, or pharmaceutically acceptable salts thereof, in amounts that are effective to inhibit the T-Cell synthesis of enzymes required for the competent replication and assembly of the Human Immunodeficiency Virus (HIV), and optionally including a synergistically effective amount of AZT or synergistically effective amounts of AZT and MISID or 3TC, or pharmaceutically acceptable salts thereof.

7. A pharmaceutical composition comprising a synergistically effective combination of a PEG-ASNase compound, Saquinavir, or pharmaceutically acceptable salts thereof, and a pharmaceutically acceptable carrier, and optionally including a synergistically effective amount of AZT or synergistically effective amounts of AZT and MISID or 3TC, or pharmaceutically acceptable salts thereof.

8. A pharmaceutical kit for treating or preventing a physiological condition associated with HIV, said kit comprising a plurality of containers, wherein at least one of said containers contains a PEG-ASNase compound or a pharmaceutically acceptable salt thereof, and at least another of said containers contains Saquinavir or a pharmaceutically salt thereof, and optionally AZT, or AZT and MISID or 3TC, or pharmaceutically acceptable salts thereof, wherein the amounts of said PEG-ASNase compounds, said Saquinavir and said optional compounds in said containers consist of a synergistically effective combination, and said containers optionally contain a pharmaceutically acceptable carrier.

9. The method of claim 1 wherein the polyethylene glycol has an average molecular weight of about 1,000 and 100,000 daltons.

10. The method of claim 9 wherein the polyethylene glycol has an average molecular weight of about 4,000 and 40,000 daltons.

11. The method of claim 5 wherein the polyethylene glycol has an average molecular weight of about 1,000 and 100,000 daltons.

12. The method of claim 11 wherein the polyethylene glycol has an average molecular weight of about 4,000 and 40,000 daltons.

* * * * *